United States Patent [19]
Tisone et al.

[11] Patent Number: 6,063,339
[45] Date of Patent: May 16, 2000

[54] METHOD AND APPARATUS FOR HIGH-SPEED DOT ARRAY DISPENSING

[75] Inventors: Thomas C. Tisone, Orange, Calif.; Christopher V. Tisone, Knoxville, Tenn.

[73] Assignee: Cartesian Technologies, Inc., Irvine, Calif.

[21] Appl. No.: 09/146,614

[22] Filed: Sep. 3, 1998

Related U.S. Application Data

[60] Provisional application No. 60/070,988, Jan. 9, 1998.
[51] Int. Cl.$^7$ .................................................. G01N 35/10
[52] U.S. Cl. .............................. 422/67; 422/63; 422/65; 422/100; 436/44; 436/50; 436/180
[58] Field of Search .................................. 422/63, 65, 67, 422/81, 100, 105, 108, 116, 119; 436/43, 44, 47, 49, 50, 55, 174, 180

[56] References Cited

U.S. PATENT DOCUMENTS

| | | |
|---|---|---|
| 2,264,564 | 12/1941 | Connor . |
| 5,056,462 | 10/1991 | Perkins et al. . |
| 5,324,480 | 6/1994 | Shumate et al. . |
| 5,334,353 | 8/1994 | Blattner . |
| 5,338,688 | 8/1994 | Deeg et al. . |
| 5,509,966 | 4/1996 | Sykes . |
| 5,593,893 | 1/1997 | Kobashi et al. . |
| 5,601,982 | 2/1997 | Sargetn et al. . |
| 5,738,728 | 4/1998 | Tisone . |
| 5,741,554 | 4/1998 | Tisone . |
| 5,743,960 | 4/1998 | Tisone . |
| 5,756,050 | 5/1998 | Ershow et al. . |
| 5,763,278 | 6/1998 | Sickinger et al. . |
| 5,770,160 | 6/1998 | Smith et al. . |
| 5,925,732 | 7/1999 | Ecker et al. .............................. 530/334 |

OTHER PUBLICATIONS

BioDot, Inc. Brochure entitled Supplier of Innovative Equipment for R&D Manufacturing of Biodiagnostic Test Kits.

(List continued on next page.)

*Primary Examiner*—Long V. Le
*Attorney, Agent, or Firm*—Knobbe Martens Olson & Bear, LLP.

[57] ABSTRACT

A dispensing apparatus and method is provided for accurately and precisely dispensing various desired patterns of reagent onto a substrate or other receptive surface or receptacle. The invention provides high-speed on-the-fly dispensing of various desired reagent patterns as provided by the operator in the form of a graphic bit map file. In one embodiment the dispensing apparatus comprises a dispensing head having an inlet end and an outlet end. The dispensing head is responsive to a first signal to dispense droplets of liquid reagent onto a substrate. The substrate or dispensing head are secured in association with a table or carriage. The table is responsive to a second signal for providing for relative X, X-Y or X-Y-Z motion between the substrate and the dispensing head. A controller is adapted to receive data representative of a desired reagent pattern and to output and coordinate the first and second signals so as to cause relative motion between the substrate and the dispensing head and, simultaneously, to cause the dispensing head to dispense droplets of liquid reagent at one or more desired locations on the substrate to form the desired reagent pattern. The controller adjusts the phase lag or lead between the first and second signals to compensate for the magnitude of relative motion between the substrate and the dispensing head given the probable trajectory of each droplet of liquid reagent. Optionally, a direct current fluid source, such as a positive displacement pump, may be provided in series with the dispensing head for precisely regulating the quantity or flow rate of liquid reagent provided to the dispensing head.

27 Claims, 16 Drawing Sheets

OTHER PUBLICATIONS

BioDot, Inc. Brochure entitled BioDot Airjet™ 2000 Dispenser.

BioDot, Inc. Brochure entitled Biojet™ Specification.

BioDot, Inc. Brochure entitled BioDot Microdoser Dispenser Series MD–1000.

BioDot, Inc. Brochure entitled CV1000 Syringe Pump Dispenser.

BioDot, Inc. Brochure entitled BioDot X–Y Membrane Handling Module with Dispensing Platform Series XY–3000.

Publication by International Business Communications, 2nd Annual Conference on Aug. 7 & 8, 1997, entitled Microfabrication & Microfluidic Technologies—Advances in the Miniaturization of Bioanalytical Devices.

User's Manual entitled Programmable Single–Chip High–Speed Pulse Generator PCL–240AK by Nippon Pulse Motor Co. Ltd.

METHOD AND APPARATUS FOR HIGH-SPEED DOT ARRAY DISPENSING

This appln. claims benefit of prov. app. 60/070,988, filed Jan. 9, 1988.

BACKGROUND OF THE INVENTION

1. Field of the Invention

The present invention relates to a method and apparatus for dispensing chemical reagents and other liquids onto a substrate such as to form a diagnostic test strip or clinical test array and, in particular, to a method and apparatus adapted for high-speed, precision dispensing of high-density "dot" arrays and other patterns onto a receptive membrane, high-density micro-well plate or other suitable receptacle.

2. Description of the Related Art

Clinical testing of various bodily fluids conducted by medical personnel are well-established tools for medical diagnosis and treatment of various diseases and medical conditions. Such tests have become increasingly sophisticated, as medical advancements have led to many new ways of diagnosing and treating diseases.

The routine use of clinical testing for early screening and diagnosis of diseases or medical conditions has given rise to a heightened interest in simplified procedures for such clinical testing that do not require a high degree of skill or which persons may conduct on themselves for the purpose of acquiring information on a physiologically relevant condition. Such tests may be carried out with or without consultation with a health care professional. Contemporary procedures of this type include blood glucose tests, ovulation tests, blood cholesterol tests and tests for the presence of human chorionic gonadotropin in urine, the basis of modern home pregnancy tests. Other tests or clinical procedures have been developed for genetic screening or genetic testing, such as for research or medical diagnostics. For example, such research or screening may be conducted via parallel testing of many individual droplets of a fluid sample on a high-density micro-well plate.

One of the most frequently used devices in clinical chemistry is the test strip or dip stick. These devices are characterized by their low cost and simplicity of use. Essentially, the test strip is placed in contact with a sample of the body fluid to be tested. Various reagents incorporated on the test strip react with one or more analytes present in the sample to provide a detectable signal.

Most test strips are chromogenic whereby a predetermined soluble constituent of the sample interacts with a particular reagent either to form a uniquely colored compound, as a qualitative indication of the presence or absence of the constituent, or to form a colored compound of variable color intensity, as a quantitative indication of the amount of the constituent present. These signals may be measured or detected either visually or via a specially calibrated machine.

For example, test strips for determining the presence or concentration of leukocyte cells, esterase or protease in a urine sample utilize chromogenetic esters which produce an alcohol product as a result of hydrolysis by esterase or protease. The intact chromogenetic ester has a color different from the alcohol hydrolysis product. The color change generated by hydrolysis of the chromogenetic ester, therefore provides a method of detecting the presence or concentration of esterase or protease, which in turn, is correlated to the presence or concentration of leukocyte cells. The degree and intensity of the color transition is proportional to the amount of leukocyte esterase or HLE detected in the urine. See, for example, U.S. Pat. No. 5,464,739.

The emergence and acceptance of such diagnostic test strips and other clinical screening methods as a component of clinical testing and health care in general has led to the development of a number of quality diagnostic test strip and clinical screening products. Moreover, the range and availability of such products is likely to increase substantially in the future.

Because test strips are used to provide both quantitative and qualitative measurements, it is extremely important to provide precision and uniformity in the placement and distribution of the reagents on the test strip substrate. The chemistry is often quite sensitive and good medical practice requires that the testing system be extremely accurate and precise as possible. When automated systems are used, it is particularly important to ensure that the test strips are reliable and that the measurements taken are quantitatively accurate.

In some cases it is necessary or desirable to provide precise patterns or dot arrays (either contiguous or non-contiguous) of reagent on a test strip, comprising different reagents and/or reagent concentrations. For example, some test strips provide multiple test areas that are serially arranged in an array so that multiple tests may be performed using a single test strip. U.S. Pat. No. 5,183,742, for instance, discloses a test strip having multiple side-by-side detection regions or zones for simultaneously performing various tests upon a single sample of body fluid. Such test strips may be used, for example, to determine levels of glucose, protein, and the pH of a single blood sample.

When such patterns (particularly overlapping and/or complex patterns) are used, it is critical that the patterns be precisely and repeatably placed on each substrate such that they may be precisely registered with a sample to be tested and/or other reagent patterns placed on the same or another mating substrate or mask. Precise registration is also required when using automated pick-and-place ("suck-and-spit") fluid handling systems. But repeatably dispensing reagents or other fluids onto a substrate in this precise manner is a highly difficult task to accomplish. The viscosities and other flow properties of the reagents, their reactiveness with the substrate or other reagents vary from reagent to reagent, and even from lot to lot of the same reagent. It is often difficult to control the dispensing apparatus to form sharp lines or other geometric shapes having uniform concentrations of reagent or other desired characteristics. It is particularly difficult provide precision and accuracy in the placement of reagent patterns on the same or different substrates. Again, this is primarily attributable to the nature of the reagents and the substrate.

Currently available dispensing methods and equipment are limited in their ability to provide the required degree of precision and accuracy, particularly on a high-speed production scale. For example, conventional reagent dispensing equipment may include a solenoid valve dispensing head mounted on or in association with a programmable X, X-Y or X-Y-Z table or carriage. The motion of the table may be electronically coordinated with the operation of the dispenser so that the dispenser can be caused to dispense one or more droplets of reagent or other fluid at any one of a number of locations on the substrate defined by the position of the X and Y axes of the X-Y table. In operation, the X-Y table moves the substrate or the dispensing head to a desired location and then stops while the dispenser is caused to dispense the desired amount of reagent onto the substrate at the desired location. After each dispensing operation is completed, the X-Y table then moves to the next location and the process repeats for as many locations as are necessary to complete the pattern.

This process of stopping and starting the X-Y table after each dispensing operation is time consuming because of the settling time of the system upon completion of each cycle. Each time the table is instructed to stop at a desired location, it takes a certain amount of time for the table or carrier platform to come to rest and for any harmonic energy in the system to be dissipated. This settling time can sometimes be as long as a few hundred milliseconds or more, depending upon the mass of the carrier platform and other system characteristics. While such a delay might not be significant for dispensing patterns of only a few dots or dispense locations, such delay becomes quite significant when complex or high-density reagent patterns are used which may be composed of as many as several thousand or more individual dots or dispense locations. This severely and undesirably limits the production speed and output of such equipment.

Conventional "stop-and-go" dispensing equipment and methods are also undesirable from a precision and accuracy standpoint. While statistical studies may be performed to determine the appropriate settling time to allot before each dispensing operation, there may be variances in the system that cannot be easily predicted or controlled. For example, the X-Y table may have a different coefficient of damping at a certain location or range of locations due to uneven wear or lubrication. In that event, an allotted settling time may be too short in some dispensing locations to allow the system to come to complete rest such that accuracy and precision are compromised. But increasing the allotted settling time only slows down production even further and, even then, does not guarantee that other variances in the system or even statistical variances will not have the same degenerative effect.

Often there may be some amount hysteresis effect or "play" in the X-Y table or carrier platform (such as caused by excessive wear), which can cause the dispensing platform to have even more imprecision when using conventional stop-and-go dispensing methods. This is because the carrier platform, when instructed to stop at a particular X-Y location, may tend to overshoot and come to rest at slightly different locations depending, for example, on what direction or at what speed the platform was traveling before it stopped. This condition can be aggravated by excessive wear and tear caused by such repetitive stop and go dispensing operations. While, some of these deficiencies may be mitigated by appropriate maintenance and control of the X-Y table, it greatly increases the difficulty of the task.

Even beyond these significant problems and limitations, current dispensing equipment and methods are often difficult to use when complex reagent patterns are desired. This is because the X-Y table and the dispensing head typically must be manually programmed and coordinated by the user to follow a predetermined series of steps and/or dispensing operations in order to achieve the desired pattern(s). This is a time consuming and repetitive task.

SUMMARY OF THE INVENTION

Accordingly, it is a principle object and advantage of the present invention to overcome some or all of these limitations and to provide an improved dispensing apparatus and method for accurately and precisely dispensing various desired patterns of reagent onto a substrate, micro-well plate or other receptive surface or receptacle. The accuracy and precision is such that the resulting patterns can be precisely registered with a sample to be tested or an automated "suck-and-spit" fluid handling system, and/or other reagent patterns placed on the same or another substrate or mask. The invention also provides for the opportunity to achieve a high degree of accuracy and precision during high-speed dispensing operations with minimal wear and tear on the dispensing equipment. The invention also allows for a dispensing apparatus and method for dispensing any one of a number of user-defined patterns on a substrate without requiring the user to manually program the dispenser or associated X-Y or X-Y-Z table.

In accordance with one embodiment of the present invention a dispensing apparatus is provided generally comprising a dispensing head secured on or in association with an X, X-Y or X-Y-Z table. The dispensing head has an inlet end and an outlet end and is responsive to a first signal to dispense droplets of liquid reagent onto a substrate. The table is responsive to a second signal for providing relative X, X-Y or X-Y-Z motion between the substrate and the dispensing head. A controller is adapted to receive data representative of a desired reagent pattern and to output and coordinate the first and second signals so as to cause relative motion between the substrate and the dispensing head and, simultaneously, to cause the dispensing head to dispense droplets of liquid reagent at one or more desired locations on the substrate to form the desired reagent pattern. A positive displacement pump or other direct-current fluid source may be provided in series with the dispensing head for precisely regulating the quantity or flow rate of liquid reagent provided to the dispensing head. Optionally, the controller also adjusts the phase lag or lead between the first and second signals in order to compensate for the magnitude of the relative motion between the substrate and dispensing head, given the distance between the dispensing head and the probable trajectory of each droplet.

In accordance with another embodiment of the present invention a high-speed precision dispensing apparatus is provided for dispensing liquid reagents onto a receptive substrate. The apparatus generally comprises a dispenser, a movable table or carriage and a controller. The dispenser is responsive to a first signal to dispense droplets of liquid reagent onto the receptive substrate. The table or carriage is responsive to a second signal to provide relative X, X-Y or X-Y-Z motion between the substrate and the dispenser. The controller is adapted to receive data representative of a desired reagent pattern and to provide the first and second signals for causing relative motion between the substrate and the dispenser while simultaneously causing the dispenser to dispense the droplets of liquid reagent at one or more desired locations on the substrate to form the desired reagent pattern. The controller also adjusts the phase lag or lead between the first and second signals in order to compensate for the magnitude of the relative motion between the substrate and dispensing head, given the probable trajectory of each droplet and the desired dispense location Optionally, a positive displacement pump or other direct current fluid source may be provided in series with the dispensing head for precisely regulating the quantity or flow rate of liquid reagent provided to the dispensing head. The syringe is responsive to a third signal which is preferably synchronized with the first and second signals.

In accordance with another embodiment of the present invention a method for high-speed precision dispensing of liquid reagents onto a receptive substrate is provided. The method comprises the steps of:

(1) receiving data representative of a desired reagent pattern;

(2) providing a first signal to a table or carriage to provide relative X, X-Y or X-Y-Z motion between the substrate and the dispenser;

(3) simultaneously providing a second signal to a dispenser to cause the dispenser to dispense droplets of liquid reagent onto the receptive substrate at predetermined locations to form the desired reagent pattern; and (4) adjusting the phase lag or lead between the first and second signals to provide a desired drop offset and/or to compensate for the magnitude of the relative motion between the substrate and the dispensing head given the probable trajectory of each droplet.

Optionally, the method further includes the step of providing a third signal to a pump device for supplying a quantity of liquid reagent to the dispenser, the pump device being hydraulically arranged in series with the dispenser so as to independently regulate the amount or flow rate of liquid reagent supplied to the dispenser.

For purposes of summarizing the invention and the advantages achieved over the prior art, certain objects and advantages of the invention have been described herein above. Of course, it is to be understood that not necessarily all such objects or advantages may be achieved in accordance with any particular embodiment of the invention. Thus, for example, those skilled in the art will recognize that the invention may be embodied or carried out in a manner that achieves or optimizes one advantage or group of advantages as taught herein without necessarily achieving other objects or advantages as may be taught or suggested herein. All of these embodiments are intended to be within the scope of the invention herein disclosed. These and other embodiments of the present invention will become readily apparent to those skilled in the art from the following detailed description of the preferred embodiments having reference to the attached figures, the invention not being limited to any particular preferred embodiment(s) disclosed.

DETAILED DESCRIPTION OF THE PREFERRED EMBODIMENTS

Figure 1:
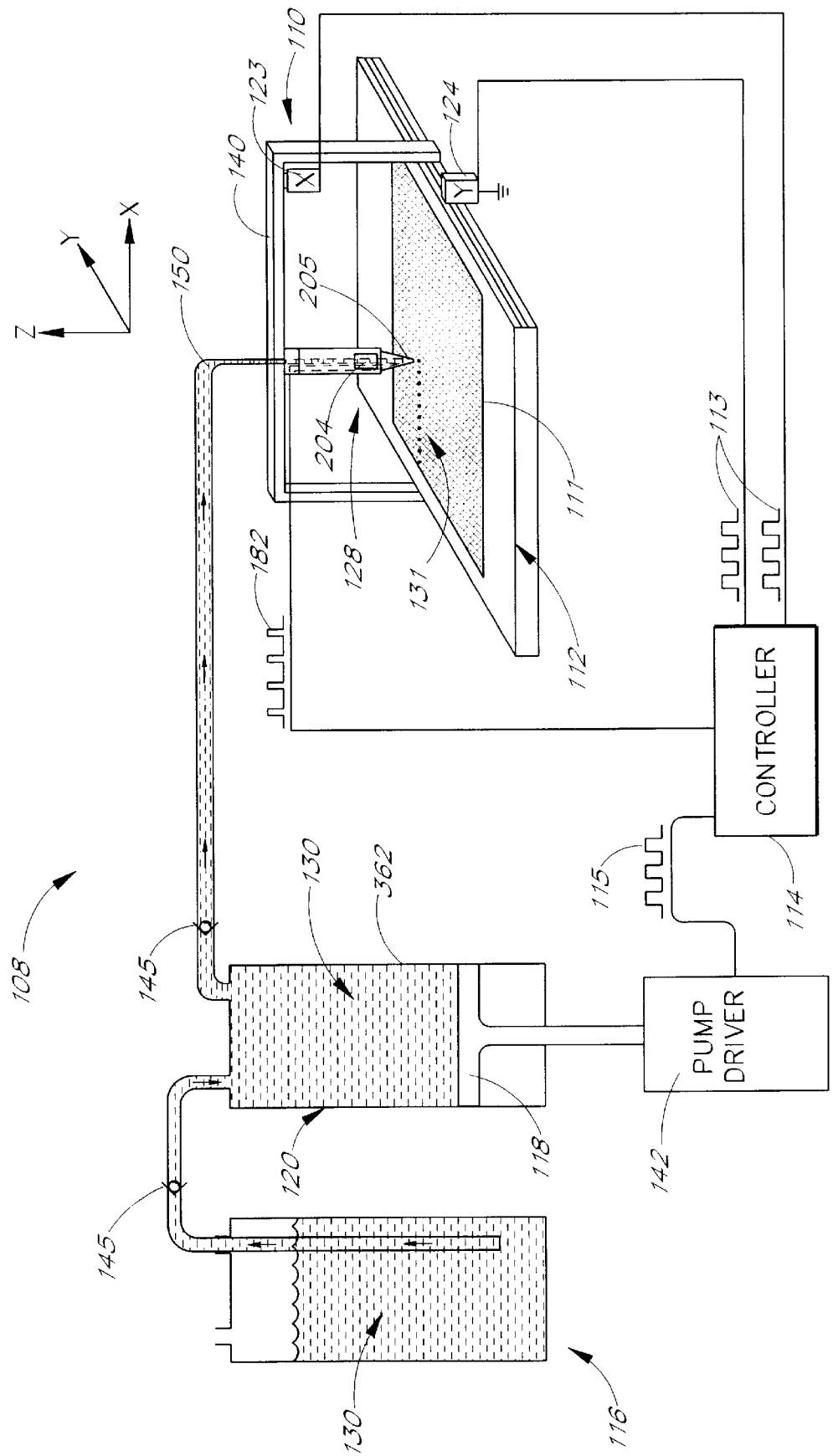
FIG. 1 is a simplified schematic drawing illustrating one embodiment of a dispensing apparatus having features and advantages in accordance with the present invention.

U.S. Pat. Nos. 5,738,728, 5,743,960 and 5,741,554, hereby incorporated by reference, first disclosed the concept of a reagent dispensing apparatus and method in which a positive displacement syringe pump is used in combination with a liquid dispenser, such as a solenoid valve dispenser or piezoelectric dispenser, to achieve improved dispensing operations. The syringe pump meters a predetermined quantity or flow rate of reagent to the dispenser to regulate the quantity or flow rate of liquid reagent dispensed. Simultaneously, an associated X, X-Y or X-Y-Z table is controlled so as to move a substrate in coordinated relation with the dispenser operation such that the reagent density can be controlled, for example, in terms of volume of reagent deposited per unit length of substrate substantially independently of the particular flow characteristics of the liquid reagent or the particular operating parameters of the dispenser (within a given range).

Prior to the advent of this invention, production flow rates would often drift during dispensing operations due to changes in temperature, humidity or changes in the viscosity or other properties of the reagent. This caused undesirable lot to lot variances of reagent coating concentrations or coating patterns. Thus, conventional reagent dispensing equipment required constant monitoring and frequent adjustment of various input parameters, such as reagent pressure, valve duty-cycle and frequency, to maintain a desired output. But, adjusting any one of these input parameters to maintain, say, a particular desired flow rate also affected other related output parameters, such as droplet size, droplet velocity or frequency. As a result, many trial-and-error adjustments were often necessary to reach a desired operating point, if such operating point could be reached at all.

Providing a positive displacement pump in series with the dispenser solved many of these problems by allowing the quantity or flow rate of reagent to be controlled independently of the particular flow characteristics of the liquid being dispensed and/or the operating parameters of the particular dispenser. For example, the size of droplets formed by a dispenser can be adjusted by changing the operating frequency (for a solenoid valve or piezoelectric dispenser) or by adjusting the air pressure or exit orifice size (for an air brush dispenser) without affecting the flow rate of reagent. Also, the reagent flow rate can be controlled without substantial regard to the system operating parameters otherwise required to achieve stable dispensing operations. The quantity or flow rate of reagent dispensed is controlled or regulated independently by the positive displacement pump. In this manner, the invention provided not only an improved method for metering and dispensing of liquids, but also added a new dimension of dispenser operation and control never before possible.

The commercial introduction and acceptance of these earlier inventions along with other collateral developments has sparked a renewed interest in the use of test strips or dip sticks for ever more complex applications, such as for high-throughput drug and/or genetic screening, medical research and other custom applications. The commercial feasibility of manufacturing such test strips on a production level has also spurred technological advances in the test strips themselves and in the associated clinical chemistries and underlying diagnostics. These advances have further enhanced the commercial and clinical acceptance and viability of such test strips for home and clinical use in a wide variety of areas.

The present invention improves and expands upon this earlier work by providing a high-speed dispensing apparatus and method for more precisely and repeatably depositing reagent onto a substrate or other receptive surface or receptacle. The disclosed apparatus and method have particular commercial advantage for dispensing complex and/or high-density patterns of reagent because it allows for precise dispensing "on-the-fly"—that is, without the need to alternately stop and start the X-Y carrier platform. As a result, higher "dot" densities, and even more complex patterns may be dispensed without significantly increasing production time or operating costs per strip. These features and advantages are made possible by combining a dispenser apparatus with a specially adapted control system which precisely coordinates dispensing operations with the motion of an X-Y table or other similar platform.

System Overview

Figure 2:
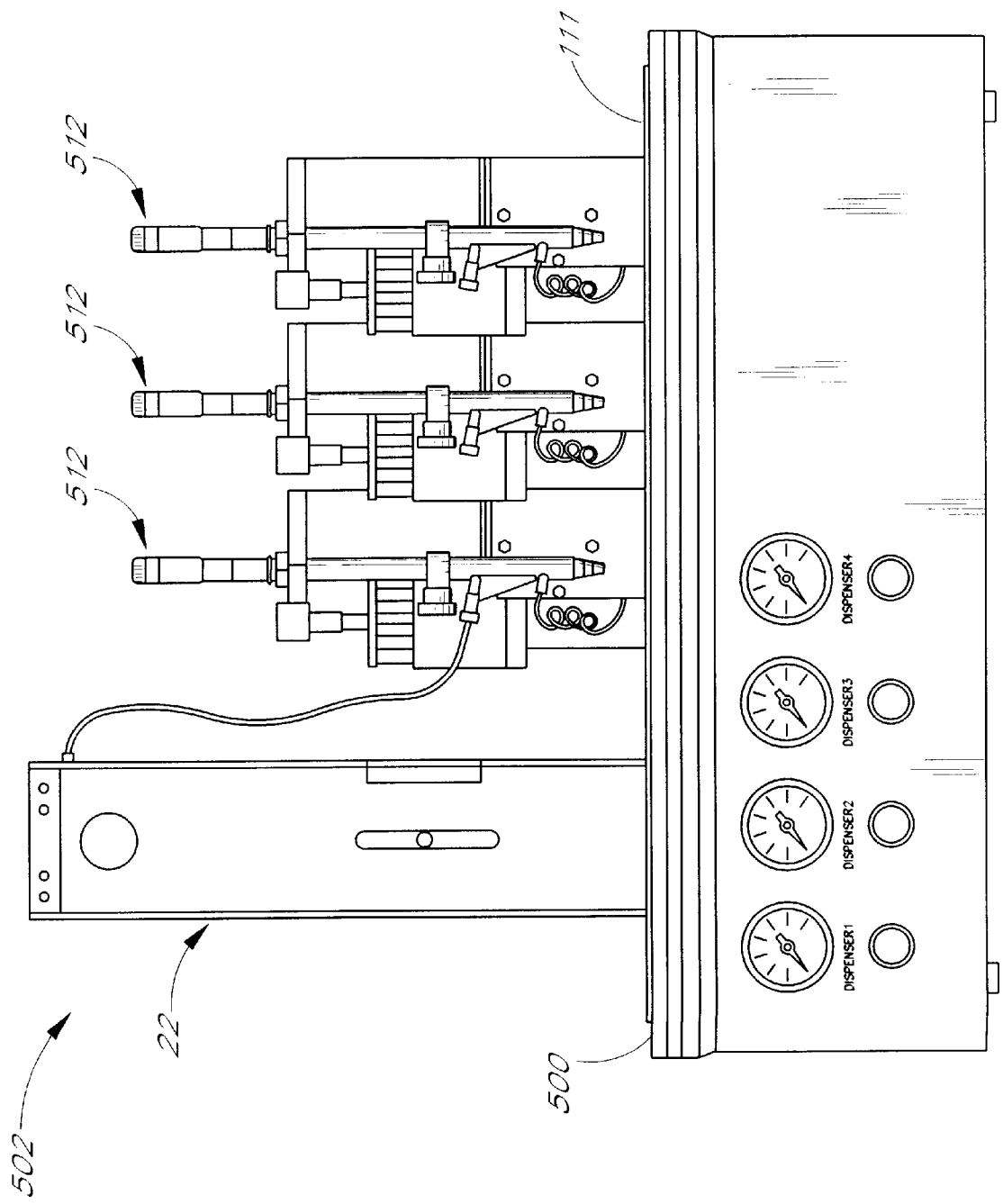
FIG. 2 is a front elevational view of an alternative embodiment of a dispensing apparatus having features and advantages in accordance with the present invention and incorporating a multi-head dispenser.

FIG. 1 is a simplified schematic overview which illustrates one embodiment of such a dispensing apparatus 108 having features and advantages in accordance with the present invention. The dispensing apparatus 108 generally comprises a dispensing head 128 having a valve or other dispensing means 204 operated by an actuator, such as solenoid. The dispensing head 128 is mounted on or in association with an X-Y table or gantry 110. Those skilled in the art will appreciate that the X-Y table 110 may include one or more position stepper motors 123, 124 or the like, which are operable to move either the dispensing head 128 and/or the carrier platform or table 112 relative to one another in the X, X-Y or X-Y-Z directions, as indicated in the drawing. It bears noting also that while only a single dispensing head 128 is shown, it is contemplated that multiple dispensing heads in linear or two-dimensional arrays can also be used with equal or improved efficacy. These may be provided and operated either in parallel as illustrated in FIG. 2 (ie. for multi-gang operation) or in another coordinated fashion, as desired.

A positive displacement pump or other direct current fluid source, such as syringe pump 120, is hydraulically coupled to a fluid reservoir 116 through a first one-way check valve 145. The syringe pump 120 draws fluid 130 from the fluid reservoir 116 and provides it to the dispensing head 128 through a second check valve 145, as shown in FIG. 1. The syringe pump 120 is operated by a syringe pump driver 142 comprising, for example, a stepper motor and an associated lead screw, for extending and retracting the piston 118 within the syringe barrel 362. Those skilled in the art will readily appreciate that when the piston 118 is retracted, reagent 130 is drawn from the reservoir 116 into the syringe pump 120. When the piston 118 is again extended, reagent 130 is forced to flow from the syringe barrel 362 into the dispensing head 128 via the supply tube 150, whereupon it is ejected by the dispensing head 128 onto the substrate 111 in the form of droplets 131.

A controller 114 oversees operation of the pump 120, X-Y table 110 (or X, or X-Y-Z table) and the dispensing head 128. Specifically, the controller 114 coordinates and controls the motion of each of the stepper motors 123, 124, and the syringe pump driver 142, as well as the opening and closing of the dispensing valve 204 to precisely dispense an amount of reagent at one or more predetermined location(s) on the substrate 111. As noted above, this dispensing operation takes place on-the-fly, that is without stopping the motion of the X-Y table. To accommodate this on-the-fly dispensing without compromising accuracy, precision or repeatability, the controller 114 calculates a phase adjustment for each dispense cycle. The phase adjustment is such as to advance (or retard) the timing of the valve opening and closing so that the dispensed droplet of reagent 131 lands at the desired location on the substrate 111 (or at a desired offset location), taking into account its anticipated trajectory.

Those skilled in the art will recognize that the magnitude of the necessary or desired phase adjustment will depend, among other things, on a number of system input and output parameters and behavioral characteristics, including the desired drop offset (if any), the vertical distance between the dispensing head nozzle 205 and the surface of the substrate 111, the velocity and/or acceleration of the dispensing head 128 and/or the substrate 111 relative to one another, the velocity of the dispensed droplets, ambient temperature and humidity, and other controlled and/or uncontrolled factors. While certain of these parameters or characteristics can be isolated and studied such that their impact on the necessary phase adjustment is fairly predictable other parameters or characteristics can neither be isolated nor predicted. The invention contemplates, however, that precise phase adjustments can be determined experimentally for a given production set up either before or during production such that a high degree of accuracy, precision and repeatability is attained during long production runs. The structure and operation of controller 114 will be described in more detail below in connection with the description of FIGS. 7–10.

Solenoid Valve Dispenser

Figure 3:
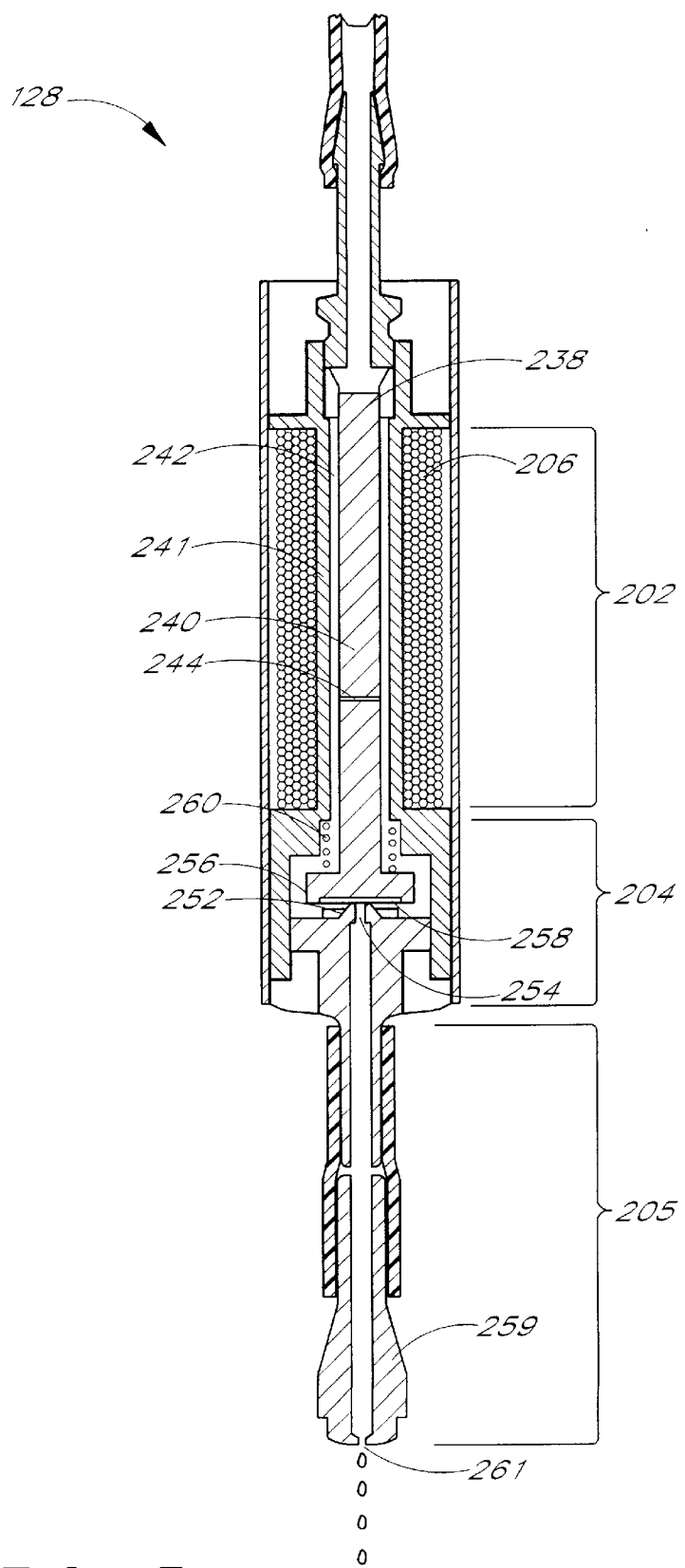
FIG. 3 is a cross-sectional view of a solenoid valve dispensing head for use in accordance with either of the embodiments of FIGS. 1 or 2.

The present invention may be implemented using any one of a number of commercially available reagent dispensers, such as air brush dispensers, piezoelectric dispensers, solenoid valve dispensers and the like. However, a solenoid valve dispenser is preferred for general applications. FIG. 3 is a cross-sectional view of a solenoid valve dispensing head 128 for use in accordance with either of the embodiments of FIGS. 1 or 2. While the selection of a particular dispensing head is not critical to practicing the present invention, it has been found that a solenoid actuated valve dispenser 128 provides good results when used in accordance with the teachings herein. Again, those skilled in the art will recognize that other types of dispensers and valve actuation devices exist and may be used with efficacy. These may include, for example, but are not limited to air brush dispensers, piezoelectric dispensers, fluid impulse dispensers, heat actuated dispensers, and the like.

Solenoid valve dispensers of the type shown in FIG. 3 are commonly used for inkjet printing applications and are commercially available from sources such as The Lee Company of Westbrook, Connecticut. The dispenser 128 generally comprises a solenoid portion 202, a valve portion 204 and a nozzle portion 205. The solenoid portion 202 comprises an electromagnetic coil or winding 206, a static core 238 and a movable plunger 240. The static core 238 and movable plunger 240 are disposed within a hollow cylindrical sleeve 241 and are preferably spaced at least slightly away from the inner walls of the sleeve 241 so as to form an annular passage 242 there between through which the reagent 130 or other liquid to be dispensed may flow. The static core 238 and movable plunger 240 are preferably formed of a ferrous or magnetic material, such as an iron alloy, and are separated by a small gap 244. Those skilled in the art will appreciate that when the solenoid coil 206 is energized a magnetic field is created which draws the plunger 240 upward toward the static core 238, closing the gap 244 and opening the valve 234.

The valve portion 204 comprises a valve seat 252, having an orifice opening 254, and a stopper 256 having a valve face 258 adapted to seal against the valve seat 252. The stopper 256 is in electromechanical communication with the plunger 240 and is spring biased toward the valve seat 252 via coil spring 260. Again, those skilled in the art will readily appreciate that as the plunger 240 moves up and down, the valve 234 will open and close, accordingly. Moreover, each time the valve 234 opens and closes, a volume of liquid is allowed to escape through the valve orifice 254. This forms an energy pulse or pressure wave which causes a droplet of liquid to be ejected from the exit orifice 261 of the nozzle tip 259.

Conventionally, a pressurized reservoir (not shown) having a predetermined constant pressure is used to force reagent or other liquid through the valve orifice 254 during the time interval (or "duty cycle") in which the valve 234 is open. Configured in this manner and under controlled conditions, such dispensers may have a repeatability as low as ±2% with a minimum drop size of about 30–35 nanoliters. The size of the droplet will be determined by the system operating parameters such as the reservoir pressure, valve open time or duty-cycle, and the viscosity and other flow characteristics of the particular reagent or liquid being dispensed. Of course, certain fixed parameters, such the size and shape of the nozzle 259 and the nozzle opening 261, will also play an important role in the operational characteristics of the valve in terms of droplet size and repeatability. In general, however, droplet size increases with increasing reservoir pressure and valve open time.

In accordance with a particularly preferred embodiment of the present invention a positive displacement pump 120 (see eg., FIG. 1) is provided in series with the solenoid valve dispenser 128. Configuring the dispensing system in this manner has the benefit of forcing the solenoid valve dispenser 128 to admit and eject a quantity and/or flow rate of reagent as determined solely by the positive displacement pump 120, with which it is hydraulically in series. For example, the syringe pump could be instructed to deliver a flow rate of 1 microliter per second of reagent to the solenoid valve dispenser 128 at a steady rate. As the valve stopper 256 is opened and closed at a given frequency and duty cycle a series of droplets are formed which will exactly match the desired flow rate. The syringe pump acts as a forcing function for the entire system, ensuring that the desired flow rate is maintained regardless of the duty cycle or frequency of the dispensing valve.

Advantageously, within a certain operating range the frequency and/or velocity of the droplets can be adjusted without affecting the flow rate of reagent simply by changing the frequency and/or duty cycle of the energizing pulses 182 (FIG. 1) provided to the solenoid valve dispenser. Of course, there are physical limitations of valve open time or duty-cycle necessary to achieve stable droplet formation. If the open time is too short relative to the flow rate, the pressure will increase and possibly prevent the valve dispenser 128 from functioning properly. If the open time is too long relative to the flow rate, then drop formation may be impaired or may not be uniform for each open/close cycle. Nevertheless, for a given flow rate of reagent 130 provided by the syringe pump 120 there will be a range of compatible frequencies and/or valve open times or duty-cycles in which stable dispensing operations may be achieved at the desired flow rate and droplet size. This range may be determined experimentally for a given production set up.

Syringe Pump

Figure 4:
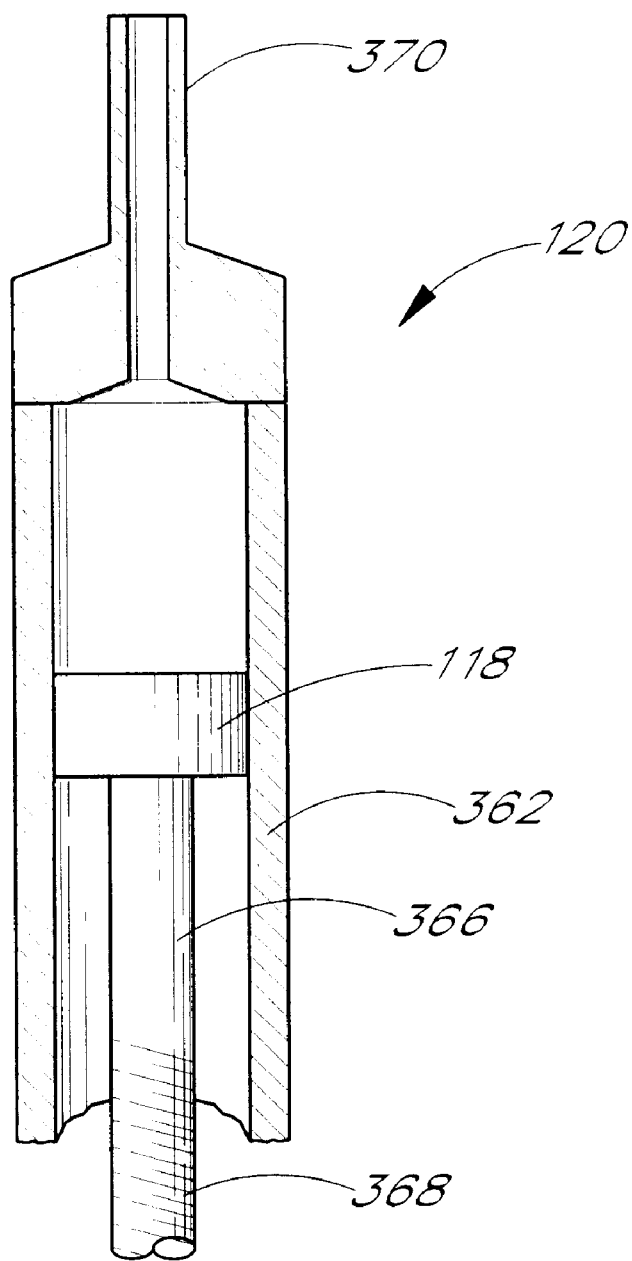
FIG. 4 is a cross-sectional view of a positive-displacement syringe pump for use in accordance with either of the embodiments of FIGS. 1 or 2.

As illustrated in FIG. 4, a suitable syringe pump 120 generally comprises a syringe housing 362 of a predetermined volume and a plunger 118 which is sealed against the syringe housing by O-rings or the like (not shown). The plunger 118 mechanically engages a plunger shaft 366 having a lead screw portion 368 adapted to thread in and out of a base support (not shown). Those skilled in the art will readily appreciate that as the lead screw portion 368 of the plunger shaft 366 is rotated the plunger 118 will be displaced axially, forcing reagent 130 from the syringe housing 362 into the exit tube 370. Any number of suitable motors or mechanical actuators may be used to drive the lead screw 368. Preferably, a pump driver 142 including a stepper motor (FIG. 1) or other incremental or continuous actuator device is used so that the amount and/or flow rate of reagent 130 can be precisely regulated.

Several suitable syringe pumps are commercially available. One such syringe pump is the Bio-Dot CV1000 Syringe Pump Dispenser, available from Bio-Dot, Inc. of Irvine, Calif. This particular syringe pump incorporates an electronically controlled stepper motor for providing precision liquid handling using a variety of syringe sizes. The CV1000 is powered by a single 24 DC volt power supply and is controlled via an industry-standard RS232 or RS485 bus interface. The syringe pump may have anywhere from 3,000–24,000 steps, although higher resolution pumps having 48,000 steps or more may also be used to enjoy the benefits of the invention herein disclosed. Higher resolution pumps, such as piezoelectric motor driven pumps, may also be used to provide even finer resolutions as desired. The lead screw 368 may optionally be fitted with an optical encoder or similar device to detect any lost steps. Alternatively, the lead screw of the metering pump can be replaced with a piezoelectric slide to provide both smaller volume increments and also faster acceleration/deceleration characteristics. Multiple syringe pumps may also be used in parallel, for example, for delivering varying concentrations of reagent 130 and/or other liquids to the dispenser or for alternating dispensing operations between two or more reagents. This could have application, for instance, to ink jet printing using one or more colored inks or liquid toners.

The travel of the plunger 118 is preferably about 260 mm. Plunger speeds may range from 0.8 seconds per stroke with a 10-step minimum for low-resolution pumping or 1.5 seconds per stroke with a 20-step minimum for high-speed resolution pumping. The stroke speed may vary depending upon the syringe size and the tubing used. Syringes may vary from less than 50 microliters to 25 milliliters, or more as needed. For most reagent dispensing applications it should be adequate to provide a syringe having a volume from about 50 microliters to about 25 milliliters. The minimum incremental displacement volume of the pump will depend on the pump resolution and syringe volume. For example, for a syringe housing volume of 50 ml and 12,000 step resolution pump the minimum incremental displacement volume will be about 42 nanoliters. Minimum incremental displacement volumes from about 0.5 nanoliters to 2.1 milliliters are preferred, although higher or lower incremental displacement volumes may also be used while still enjoying the benefits of the present invention.

The syringe housing 362 may be made from any one of a number of suitable bio compatible materials such as glass, Teflon™ or Kel-F. The plunger 118 is preferably formed of virgin Teflon™. Referring to FIG. 1, the syringe 120 is connected to the reservoir 116 and the dispensing head 128 using a Teflon tubing 150, such as ¼-inch O.D. tubing provided with luer-type fittings for connection to the syringe and dispenser. Various check valves 145 may also be used, as desired or needed, to direct the flow of reagent 130 to and from the reservoir 118, syringe pump 120 and dispenser 128. Of course, a wide variety of other positive displacement or "direct current" fluid sources may also be used to achieve the benefits and advantages as disclosed herein. These may include, for example and without limitation, rotary pumps, peristaltic pumps, squash-plate pumps, pumps incorporating hydraulic or electronic feedback control and the like.

Controller

Figure 7:
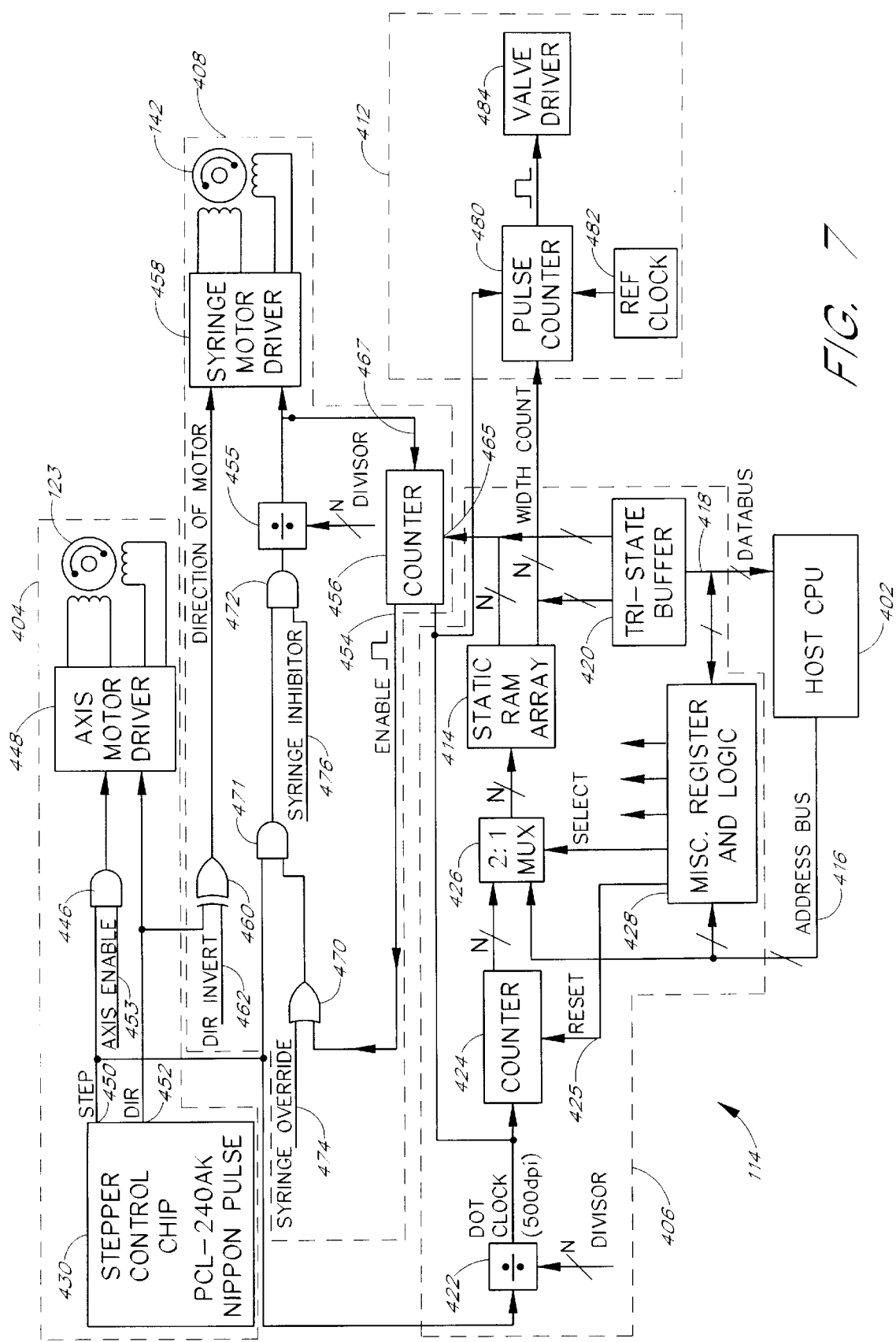
FIG. 7 is a detailed partial schematic circuit diagram of a control system for a reagent dispensing apparatus having features and advantages in accordance with the present invention.

FIG. 7 illustrates one possible embodiment of an electronic controller 114 having features of the present invention. The controller 114 of the embodiment described herein generally comprises a host CPU 402 or computer which interfaces with some form of data memory. In particular, the controller may be roughly divided into five basic subsystems: host CPU 402, coordinate control circuitry 404, memory and logic circuitry 406, syringe stop count circuit 408, and valve firing circuit 412. Each of these subsystems are illustrated schematically by phantom lines in FIG. 7 and are described in more detail below. Those skilled in the art will appreciate that each subsystem works in cooperation with the other subsystems to simultaneously control the coordinate stepper motors 123, 124, the syringe pump motor 142 and the solenoid valve dispenser 128 (FIG. 1) to achieve the desired dispensing.

Host CPU

A host CPU 402 serves as the central controller and also the interface between the controller 114 and the user. It allows the operator to input dispensing data and to control, either independently or simultaneously, each aspect of the dispensing apparatus 108 (FIG. 1).

In the particular embodiment illustrated herein, the host CPU 402 generally comprises a 80×86 or Pentium-based computer having a slot or bus compatible to accept a plug-in circuit board. The circuit board or "controller card" contains the four subsystems shown in FIG. 7. The controller card mounts or plugs into a computer bus providing data transfer and communication of instructions. The host CPU 402 also provides power to the controller card and further allows an operator to access, program and control the functions of the controller card. It is further contemplated that the host CPU 402 contains suitable computer software compatible with the host CPU and the controller card which facilitates operation of the system as described herein.

Preferably, a display device and data input means are integral with the host CPU 402 thereby providing means to input data into a memory or static RAM array 414 located on the controller card and to verify the same using the display device. As is known by those of ordinary skill in the art, a keyboard, mouse, trackball, light pen, capacitance touch screen, computer storage media are all acceptable data input means. Likewise, a color video monitor or screen provides a suitable display means. Using a data entry device, such as a keyboard, an operator may enter data into the host CPU 402 in the form of a data array or graphical bit map to thereby instruct the electronic controller and dispensing apparatus of the desired reagent pattern and characteristics. Conventional computer software may facilitate the entry of the data array or bit map via the host CPU 402 to the memory 414 of the controller card.

In the particular preferred embodiment described herein, the controller card is compatible with a PC-AT clone, i.e. 80×86 or Pentium-based architecture. The controller card form factor and bus configuration match a PC-104 format, thereby allowing the circuit design to be quickly and inexpensively manufactured in a circuit board format. In the particular preferred embodiment shown and described above, the host CPU 402 utilizes a Motorola 68332 processor as the main microprocessor. However, as known by those skilled in the art, other computer systems and host CPU's may be used with equal advantage.

For the purposes of the present application, a bus comprises an electrical connection which facilitates the exchange of information, such as address information, data information and/or instructions. The present invention includes an address bus 416 which carries address information, and a data bus 418 which carries data information. The data bus 418 and the address bus 416 connect to the memory and logic circuitry 406. Advantageously, the data bus 418 and the address bus 416 are bi-directional thereby allowing the transfer of data between the controller card and the memory and logic circuitry 406. Thus, the controller 114 may display status information from the controller card on the video display of the host CPU 402 or alternatively, write the information to a data file on a permanent storage medium. As is known to those of ordinary skill in the art, other types of electrical connections exist which carry electronic information and are fully contemplated for use with the present invention.

Memory and Logic Circuitry

Connected to the host CPU 402 is a network of circuitry referred to herein as the memory and logic circuitry 406. In general, the memory and logic circuitry 406 stores the data which defines the desired dispensing pattern and characteristics. Other hard-wired logic circuitry, such as a counter 424 and multiplexer 426, may also be used, as desired, to parse dispensing data to the other subsystems of the controller 114 or to speed up the processing of information and control data.

In particular, the memory and logic circuitry 406 generally comprises an electronic memory 414 for storing data regarding reagent 130 dispense parameters, a tri-state buffer 420, a divisor 422, an address counter 424, a multiplexer 426 and various logic circuitry to assure proper operation of the electronic controller 114. The tri-state buffer 420 connects to the host CPU 402 via the data bus 418 and serves to isolate the CPU from the controller card. The buffer is adapted to rapidly accept and store data to further increase data transfer speed and free the host CPU 402 of data transfer operations.

In turn, the tri-state buffer 420 connects to a memory module 414, preferably a static ram array. The tri-state buffer 420 also connects to the output lines of the static ram array 414 for direct control of the syringe motor 142 and the solenoid valve dispenser 128 (FIG. 1).

The static ram array 414 comprises an electronic memory device which stores the data in the form of a data array sent from host CPU 402 via the tri-state buffer 420. The data array 414 defines the reagent 130 dispensing pattern. Advantageously, access to each value in the data array 414 corresponds to a data array address thereby allowing access to specific data in the data array.

A 2:1 multiplexer 426 connects via the address bus 416 to the host CPU 402 The 2:1 multiplexer 426 allows the operator to select which of the two inputs pass the the output. The multiplexer 426 has two inputs: a first input which connects to the output of the counter 424 and a second input which connects to the address bus 416 In the preferred embodiment, the multiplexer 426 provides a data array address from the host CPU 402 or, during steady state operation, from the output of the memory and logic circuitry counter 424. Those skilled in the art will recognize that when the multiplexer 426 passes the counter output to the static RAM array 414, the address increments automatically by way of a stepper control chip output. The output of the stepper control chip 430 advantageously serves as the main clock for the controller and thereby synchronizes operation of the system 108. A more detailed discussion of the stepper control chip 430 is provided below.

The counter output 424 provides one of the two inputs to the multiplexer 426. As known by those of ordinary skill in the art, a counter 424 comprises digital logic circuit which records input pulses to produce a binary word that increases or decreases in value by a predetermined number (preferably 1) upon each input pulse. This binary word provides the next address for retrieving data from the data array. Thus, the counter 424 operates to increment the address of the data array 414. The counter 424 is preferably a resettable circuit and a reset line 425 is provided from the miscellaneous register and logic 428 to reset the counter 424. The counter 424 may also be reset either automatically or manually via an interrupt (not shown) from the host CPU 402.

The output of divisor circuitry 422 provides input to the counter 424. The divisor 422 provides an output after receiving N number of input pulses, where N is the number of input pulses required to trigger an output pulse. If desired, the divisor 422 can be user adjustable so that the value for N may be set by the operator. Thus, the resolution of the dispensing apparatus may be controlled by the number of pulses output by the stepper control chip 430 and the value assigned to N. As known by those of ordinary skill in the art, a divisor 422 can readily be implemented using a form of a counter circuit wherein the counter circuit outputs a pulse upon receipt of a certain number of input pulses. The input to the divisor 422 is the main clock signal provided by the stepper control chip 430. The divisor circuit 422 also provides output to the syringe stop count circuit 408 and the valve firing circuit 412, described below.

Dual output lines from the static ram array 414 connect to each of the syringe stop count circuit 408 and the valve single shot circuit 412, both of which are described in more detail below. Those skilled in the art will appreciate that the output of the static ram array 414 defines the desired syringe motor increment and the valve pulse duration and is sequentially incremented by the address counter input.

To facilitate operation, miscellaneous registers and logic, shown at step 428, are integral with the above described componentry. As known by those of ordinary skill in the art, various logic circuitry and storage registers 428 are interspersed with the componentry described herein as appropriate. Alternatively, much of the electronic hardware described herein could easily be embodied through the use of suitable software, as desired or appropriate.

Coordinate Control Circuitry

Coordinate control circuitry 404 moves the dispensing head 128 (FIG. 1) to each desired location. While FIG. 7 only shows circuitry for X axis motion control, those skilled in the art will readily appreciate that Y axis motor control is also contemplated with the present invention to facilitate operation with an X-Y table. In another embodiment, the controller 114 may also incorporate Z axis motion to achieve compatibility with an X-Y-Z table. This provides additional control of the system by providing means to vary the distance between the dispensing head 128 and the substrate 111 (FIG. 1).

The coordinate control circuitry 404 generally comprises a stepper control chip 430, control logic 446 and an axis motor driver 448. As discussed in greater detail below, the coordinate control circuitry 404 provides input to the divisor 422 of the memory and logic circuitry 406. The coordinate control circuitry 404 also provides control of an axis stepper motor 123 (FIG. 1) and input to the syringe stop count circuit 408 and the valve firing circuit 412.

The stepper control chip 430 generates a constant step pulse output. This step pulse output serves dual purposes. First, the step pulse provides a control signal to the axis motor drive 443 which in turn powers the stepper motor 123. The stepper motor controls the dispensing head position along the X-axis. Second, the step pulse, or a divided form thereof, propagates throughout the system as the main clock pulse. The stepper control chip 430 is of the type often used to operate stepper motors. The preferred embodiment described herein utilizes a Nippon Pulse PCL-240AK available from the Nippon Pulse Motor Co., Ltd, although other stepper motor control chips are currently available and are operational with the invention disclosed herein.

Moving now in more detail to the coordinate control circuitry, the stepper control chip 430 has two outputs: a step pulse output 450 and a direction signal output 452. The first output, the step pulse output 450, connects to at least one logic device to regulate the operation of the step motor 123. In this embodiment the logic device comprise a dual-input AND gate 446. One input of the AND gate 446 connects to the step pulse output 450 from the stepper control chip 430. An axis enable line 453 connects to the other input of the AND gate 446. The axis enable signal, when high, allows the step pulse output to propagate to the output of the AND gate 446. The memory and logic circuitry 406, described above, provides the axis enable signal to the AND gate 446 thereby providing means to cease movement of the dispensing head 128, either automatically via the data array or manually via the host CPU 402.

The second output of the stepper control chip 430, the motor direction control signal, is provided on a direction control line 452 to control the direction of the X axis stepper motor 123. The motor direction line 452, which carries the motor direction signal, connects directly to the axis motor driver 448. The stepper motor direction signal is also fed to the syringe stop count circuit 408, described in more detail below. Changing the state or logic level of the direction line, changes the direction of the X-axis stepper motor 123. This advantageously provides for bidirectional printing which, as noted above, speeds dispensing operation.

An axis motor driver 448 receives the output from the AND gate 446 and the stepper control chip 430. The axis motor driver 440 is an electronic device controlled by normal logic level signals which correlates the logic level input signals into a specialized output having increased current sourcing ability to drive a stepper motor. As is known by those of ordinary skill in the art many different axis motor drivers are available which satisfy the needs of the current invention.

The output of the axis motor driver 448 is provided to the X-axis stepper motor 123. The stepper motor 123 controls movement of the dispensing head 128 in relation to the substrate 111 (FIG. 1). Preferably, the stepper control chip 430, axis motor driver 448, and stepper motor 123 have resolution of greater than about a hundred steps per linear inch, more preferably greater than about five hundred steps per linear inch, even most preferably greater than about seven hundred fifty steps per linear inch.

Syringe Stop Count Circuit

The syringe stop count circuit 408 controls the syringe 120 based on signals received from the stepper control chip 430 and the memory and logic circuitry 406. The syringe stop count circuit 408 comprises control logic, a syringe circuit divisor 455, a syringe circuit counter 456, and a syringe motor driver 458. Advantageously, the syringe stop count circuit 408 is synchronized with the other subsystems of the controller 114 to ensure precise and synchronized control over syringe motor driver 458.

The control logic provides means to obtain manual control over the syringe and includes a direction control NOR gate 460 which has two inputs, the first of which connects to the direction line 452 of the stepper control chip 430 and the second of which connects to a syringe direction invert line 462. The syringe direction invert line 462, although not shown, connects to the memory and logic circuitry 406 and is discussed in more detail below. The output of the direction control NOR gate 460 connects to the syringe motor driver 458, described below. Based on the signals entering the NOR gate 460 the syringe motor driver can be made to change the direction of the syringe stepper motor 142. Advantageously, the syringe motor 142 is bi-directional thereby providing means to draw liquid into the syringe or expel liquid from the syringe 120. The syringe direction invert signal may be provided, for example, in accordance with data contained in the static ram array 414 and thus may operate based on initial programming.

If the direction of the stepper chip 430 reverses direction, then the motion of the syringe plunger 118 (FIG. 1) also reverses direction. However, the values in the static ram array 414 may exist to ensure bi-directional printing, i.e. the level of the signal on the direction invert line 462 changes when the direction of the stepper motor 123 changes. Alternatively, an operator may manually control the direction of the syringe 120 (FIG. 1) through the host CPU 402 via the direction invert line 462. Manual control over the syringe 120 (FIG. 1) provides the operator with the ability to aspirate, dispense or fill the syringe 120 to achieve unique dispensing operations on a non-automated basis.

The syringe stop count circuit 408 also contains a syringe circuit counter 456. The syringe circuit counter 456 determines the number of pulses to be provided to the syringe motor during a discreet dispense operation. In the present embodiment, the syringe circuit counter 456 has three inputs 465, 466, 467 and an output 464. The first input 465 accepts the syringe increment value from the static RAM array 414. The syringe increment value is the number of steps the syringe motor 142 (FIG. 1) will move at a particular target location. The second input 466 accepts the output of the divisor 422 from the memory and logic circuitry divisor 422.

The divisor output acts as the main clock for the syringe circuitry counter 456 thereby synchronizing the counter's output to each rising pulse of the divisor output. The counter's third input 467 is a tap to monitor the pulses arriving at the syringe motor driver 458 and thereby count down the value at the counter. Thus, the syringe circuit counter 456 obtains a value from the data array, in this case the number of steps the syringe 120 is to increment, and in response to each upward edge of the main clock signal, provides an equal number of pulses to an output 454.

The output 454 of the counter 456 feeds to the three part logic network of the syringe stop count circuit 408. In general, the logic network synchronizes operation of the syringe 120 (FIG. 1) with the position stepper motor 123 and provides manual control for a user to inhibit operation of the syringe. The logic network comprises a syringe override OR gate 470, an AND gate 471, and a syringe inhibitor AND gate 472. The syringe override OR 470 gate has a first input connected to the counter output 454 described above. The syringe override OR gate 470 has a second input connected to a syringe override signal line 474, which provides means to manually operate the syringe motor 142. The data array in the static RAM array 414 may provide the syringe override signal, or alternatively, in manual control mode, the host CPU 402 may provide the syringe override signal via the memory and logic circuitry 406.

The output of the syringe override OR gate 470 connects to a first input of an AND gate 471. The second input of the AND gate connects directly to the output of the stepper control chip 430. The AND gate 471 allows for syringe motor signal propagation from either the syringe override signal or, during automatic operation based on the values from the static ram array 414. The output of the AND gate 471 connects to a first input of a syringe inhibit AND gate 472. The second input to the syringe inhibit AND gate 472 comprises a syringe inhibit signal line 476, which provides means to cease operation of the syringe motor 142. The data array in the static RAM array 414 provides the syringe inhibit signal, or when the dispenser is under manual control, the host CPU 402 provides the syringe inhibit signal.

The output of the syringe inhibit AND gate 472 enters a syringe circuitry divisor 455. The divisor 455 is identical to the divisor described above in the memory and logic circuitry 406, and thus is not described in detail again. The divisor 455 provides an output pulse for every N number of input pulses, when N determines the resolution of the system. The divisor 455 provides its output to the syringe circuitry counter 467 and the input of the syringe motor driver 458.

The syringe motor driver 458 operates substantially in accordance with the principles of the previously described axis motor driver 448 of the coordinate control circuitry 404 and therefore will not be repeated here.

It was stated above that providing a positive displacement pump 120 in series with the solenoid valve dispenser 128 (see FIG. 1) has the benefit of forcing the solenoid valve dispenser 128 to admit and eject a quantity and/or flow rate of reagent as determined solely by the positive displacement pump 120. In essence, the syringe pump acts as a forcing function for the entire system, ensuring that the desired flow rate is maintained regardless of the duty cycle, frequency or other operating parameters, of the dispensing valve. That is certainly true for steady-state operation.

However, for non-steady-state operation, such as during initial start-up or for intermittent dispensing operations, transient pressure variations may occur in the supply line 150 due to hydraulic "capacitance effect", leakage or the precipitation of small gaseous bubbles within the hydraulic system. These pressure variations can cause transient or intermittent variations in the rate of fluid dispensed. For example, FIG. 5 line 910 illustrates transient dispense effects caused by initial start-up operation of a dispensing apparatus. To compensate for these variations and to ensure uniform dispensing operation during initial start-up and intermittent dispensing operations, the controller of the present invention preferably provides pre-pressurization of the supply line 150 prior to initiating dispensing operations.

Figure 5:
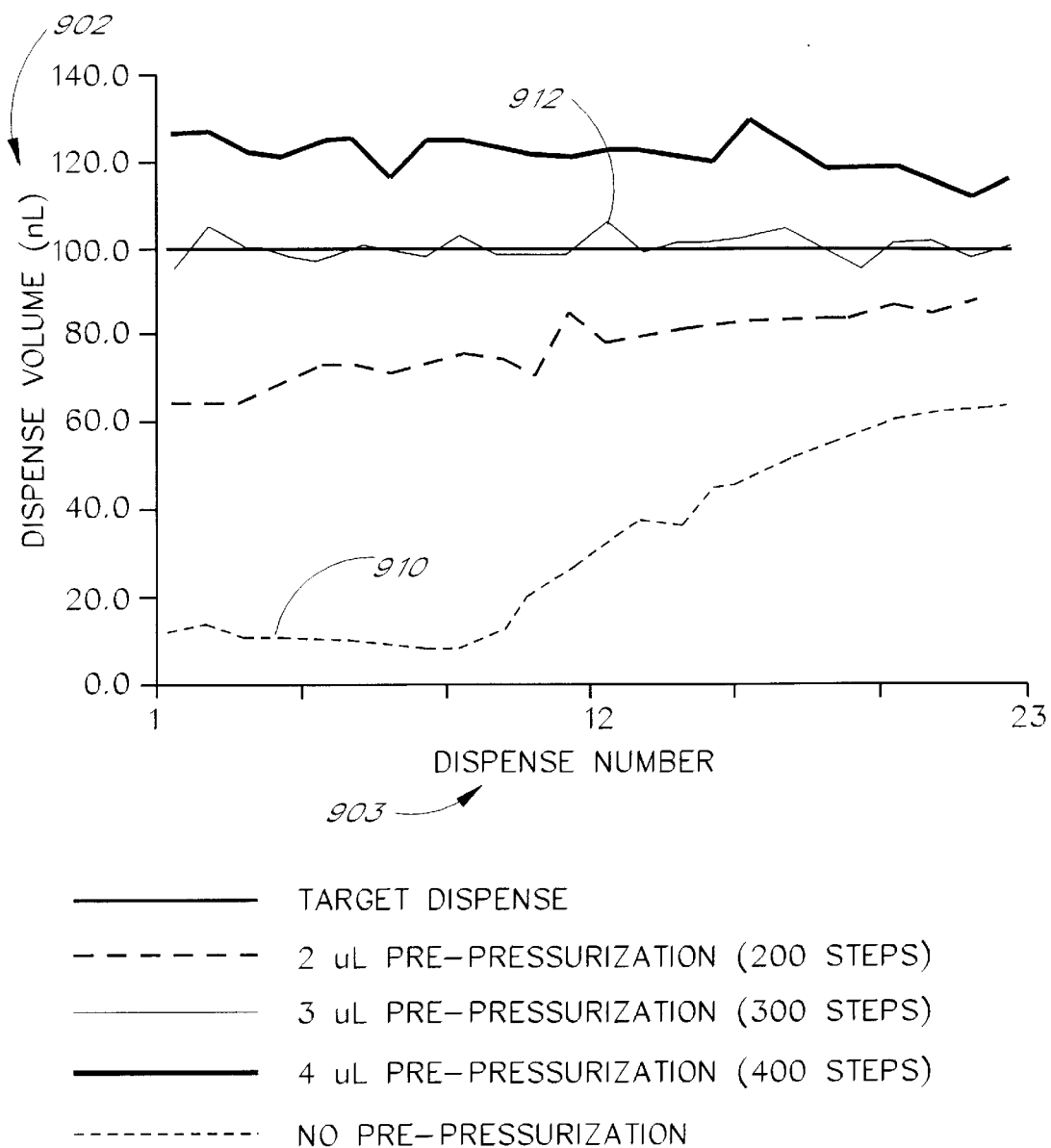
FIG. 5 is a graph illustrating initial (non-steady-state) dispense volumes versus target dispense volumes for a reagent dispensing method and apparatus in accordance with one preferred embodiment of the invention and showing the effects of reagent pre-pressurization.

Pre-pressurization may be achieved, for example, by advancing the syringe 120 while the valve 204 (FIG. 3) is closed in order to build up pressure in the line 150 to its predetermined steady-state level. Accordingly, when the valve 204 opens, the reagent 130 exits the valve at the desired target or steady-state rate or velocity. The amount of pre-pressurization needed to achieve steady-state operation can be determined empirically for a given production set-up. For example, FIG. 5 illustrates the effect of varying amounts of pre-pressurization on start-up transient dispensing operations. Alternatively, those skilled in the art will recognize that other pressure compensation techniques may also be used with efficacy, such as pressure sensor(s), time-domain compensation, syringe displacement compensation and the like.

Valve Firing Circuit

Valve firing circuit 412 controls and synchronizes operation of the dispensing head 128 in coordination with the remaining subsystems of the dispensing apparatus 108 (FIG. 1). In this embodiment the valve firing circuit 412 comprises a valve pulse counter 480, a reference clock 482, and a valve driver 484. The valve firing circuit 412 obtains two input signals. The first input, from the memory and logic circuitry 406, comprises a valve pulse value from the static RAM array 414. The valve pulse value is the time or number of click cycles the valve is to remain open. The second input comprises the main clock pulse from the output of the memory and logic circuitry divisor 422. The main clock pulse serves to synchronize operation of the valve with the rest of the dispensing apparatus. The pulse counter 480 is responsible for providing the proper pulse duration to the valve driver 484.

Advantageously the valve firing circuitry includes a reference clock. The reference clock generates pulses of constant time duration. These pulses of constant time duration provide a known time reference on which the counter may base its operation. Since the valve pulse duration is in units of time, the reference clock 482 ensures accurate operation of the dispensing head 128 (FIGS. 1, 3).

The output of the pulse counter 480 connects to a valve driver 484. The valve driver 484 receives the logic level input from the pulse counter 480 and provides a driving voltage for driving a solenoid or other such device to open and close the valve 204 of the solenoid valve dispenser 128 (FIG. 3). Accordingly, the valve driver 484 electrically communicates with the solenoid valve dispenser 202.

Software/Flow Charts

Figure 8:
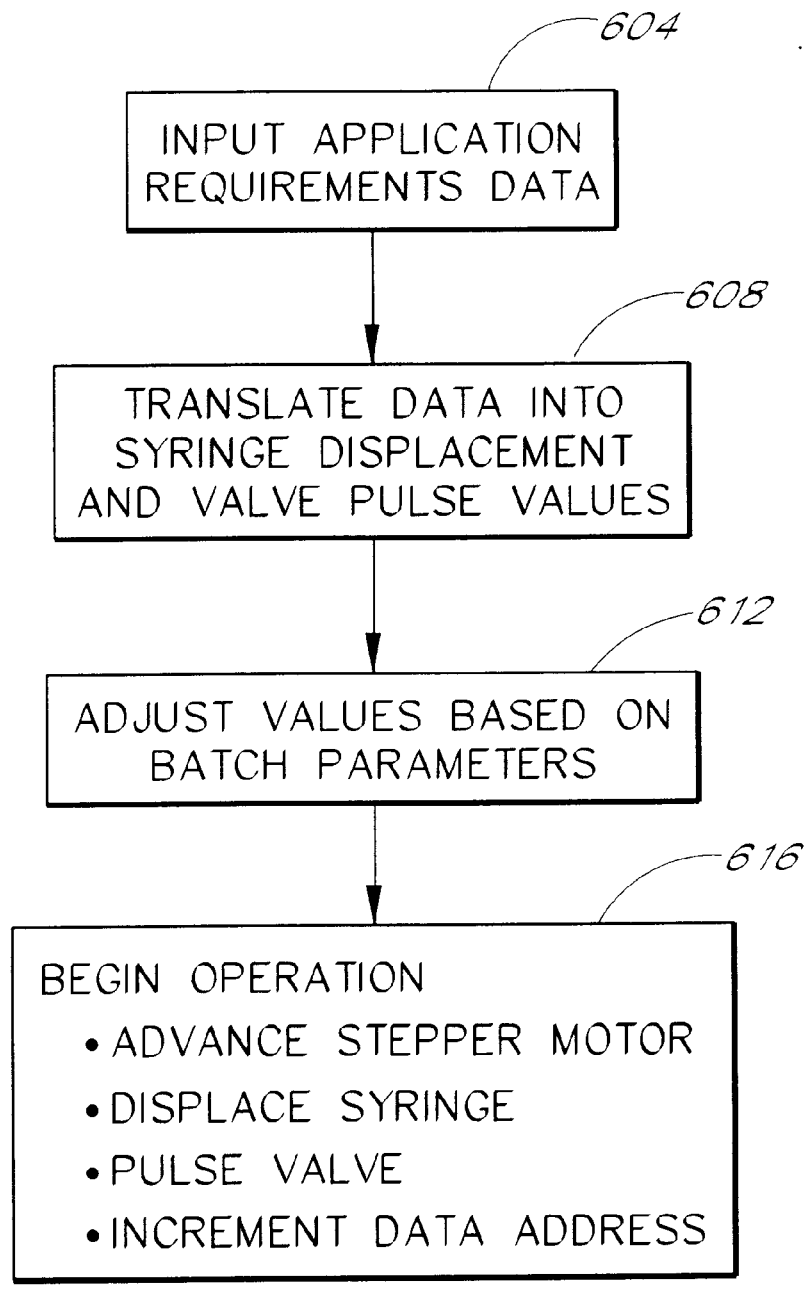
FIG. 8 is a simplified flow chart illustrating a preferred mode of operation of a dispenser apparatus having features and advantages in accordance with one embodiment of the present invention.

FIG. 8 is a flow chart illustrating the basic operation of a dispenser apparatus and control system as described herein. The first step 604 comprises providing the reagent pattern and application requirements/parameters to the controller. As mentioned above, the data is preferably entered in table or graphic form in a data file or bit map graphic file. The reagent application requirements define the location and amount and the application characteristics of the dispensing process. This may be inputted by the operator via a keyboard or graphic interface or it may be loaded directly from a storage media, such as magnetic disk or tape. At the next step 608 the system translates the application requirements into syringe displacement and valve pulse duration values and arranges the calculated values in a data array.

An example of the type of data contained in the data array is shown below as TABLE 1. For example, the data array may contain data values which govern the manner in which reagent is dispensed at a particular target location. Thus, each data address corresponds to a target location and consequently each target location has a plurality of corresponding values which define the dispensing characteristics for that location.

TABLE 1

| DATA ADDRESS | 1 | 2 | 3 | 4 | 5 | 6 | 7 | 8 | ... |
|---|---|---|---|---|---|---|---|---|---|
| SYRINGE INCREMENT VALUE | | | | | | | | | |
| VALVE PULSE VALUE | | | | | | | | | |
| X AXIS DIRECTION | | | | | | | | | |
| Y AXIS DIRECTION | | | | | | | | | |
| X AXIS VELOCITY COMPENSATION | | | | | | | | | |
| Y AXIS VELOCITY COMPENSATION | | | | | | | | | |
| SYRINGE DIRECTION INVERT | | | | | | | | | |
| SYRINGE OVERRIDE | | | | | | | | | |
| SYRINGE INHIBIT | | | | | | | | | |
| VALVE OVERRIDE | | | | | | | | | |
| PULSE INHIBIT | | | | | | | | | |
| REAGENT TEMPERATURE COMPENSATION | | | | | | | | | |
| REAGENT VISCOSITY COMPENSATION | | | | | | | | | |

The syringe displacement value and the valve pulse value for each dispense location corresponds to an address in the data array. Thus, as the controller 114 (FIG. 1) moves the dispensing head 128 across the substrate 111, the address in the data array is sequentially incremented thereby progressing through the values in the data array. This provides precise control over the amount of reagent and the manner in which the reagent is provided to each location on the substrate 111. All of this occurs simultaneously with the continuous motion of the dispensing head as it travels across the substrate.

Additional data manipulation may occur at step 612 in order to incorporate particular dispensing requirements, parameters or adjustments to aid in the reagent dispensing process. Adjustments may include estimated adjustments for fluid viscosity, fluid temperature, dispensing apparatus configuration, substrate composition and other parameters. Adjustments may also include compensation for the velocity of dispensing head for X-axis and/or Y-axis travel. For example, if the dispensing head is moving at a high velocity, the pulsing of the valve and syringe must be phased slightly ahead of the desired dispensing location in order to hit the desired target area given the anticipated trajectory. Likewise, a more viscous liquid may require additional phase adjustments or an increase in the valve pulse time and the syringe increment distance so that the proper amount of reagent exits the valve.

Many of these adjustments may be determined through empirical studies and/or experimentally for a given reagent or production set-up. For example, rough adjustments can be made to the dispense data based on known or determined parametric equations or look-up tables in order to adjust for temperature, viscosity, height or speed of the dispensing head, etc. Finer adjustments can then be made experimentally for a given production set up. This can be done, for example, by programming the dispensing apparatus to dispense known patterns of crossing or parallel lines, target patterns and/or the like, at particular locations on the substrate. By inspecting the resulting patterns, certain adjustments, such as phase lead or lag, can be made to the dispense data to compensate for noted errors. The experiment can be repeated as many times as needed. Optionally, sensors may be provided, such as temperature probes, viscosity sensing devices or other sensor devices, in order to provide real time automated feedback and adjustment of the dispenser.

Finally, at step 616, the controller aligns the reagent dispensing head in its starting position. When the dispensing apparatus begins operation, the dispensing head 128 traverses the substrate. Concurrently, the controller 114 (FIG. 1) increments the syringe 120 (FIG. 1), pulses the solenoid valve dispenser 128 (FIGS. 1, 3) and successively increments the data array address to provide precision on-the-fly reagent dispensing.

Figure 9A:
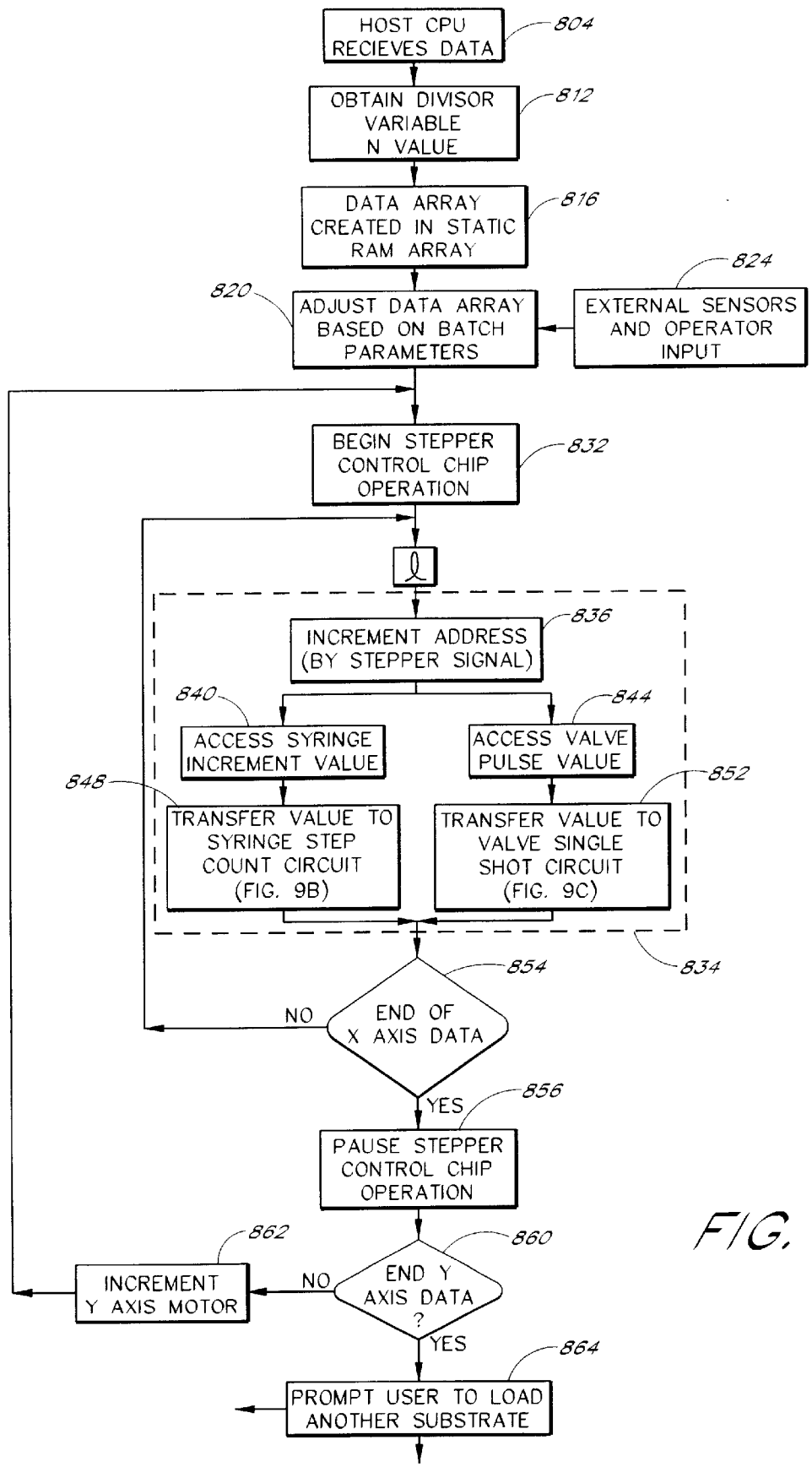
FIGS. 9A–C are detailed flow charts illustrating in more detail the preferred mode of operation of a dispenser apparatus having features and advantages in accordance with one embodiment of the present invention.

FIG. 9A is a flow chart illustrating, in more detail, one preferred mode of operation of a dispenser apparatus in accordance with the present invention. At step 804, the host CPU 402 (FIG. 7) receives data which governs the dispensing for a particular reagent and dispensing operation. A kROM, or other data entrskette, CD-ROM, or other data entry device may provide this information to the host CPU 402. The host CPU 402 or controller 114 also receives the value by which the main clock signal will be divided (represented above by the letter N), step 812. This generally determines the resolution of the dispensing operation in terms of the number of addressable target areas per linear distance "d".

At step 816 the host CPU 402 transfers the dispensing data to the static RAM array 414 (FIG. 7) of the electronic controller. The host CPU 402 in conjunction with the static RAM array 414 places the data into a data array. The data array contains the dispensing data for each target location 706 (FIG. 3) and is accessed via a data address location. The data array may also contain specific control information such as syringe inhibit, syringe override, valve inhibit, valve override and stepper motor direction, if such information is applicable, and/or various adjustments.

At step 824, the system controller 114 monitors the external sensors and/or operator input. Monitoring the external sensors may reveal additional information such as fluid viscosity and/or temperature. Based on the data from the external sensors and any final changes from the operator, the controller 114 adjusts the data array at step 820. For example, if the reagent is determined to be of higher than normal temperature, the valve duly cycle may be adjusted downward to ensure the proper amount of reagent is expelled.

At step 832, the stepper control chip 430 (FIG. 7) begins operation by outputting a series of pulses. The stepper control chip 430, or some other equivalent output device provides a pulse to the X axis driver 448 (FIG. 7) thereby actuating the X-axis stepper motor 123 (FIG. 1) which continuously moves the dispensing head 128 (FIG. 1) across the substrate 111. In the present embodiment the dispensing head 128 (FIG. 1), assumes a site of continual steady-state motion because of the high definition of the steps. In this particular embodiment the divided stepper control chip output pulses serve as the main clock for the controller 114 of FIG. 7. However, other types of system synchronizers exist and are known by those of ordinary skill in the art. For example, if the invention claimed herein is embodied using computer software, the main computer clock or a divided version thereof may serve as the synchronizing signal.

Next the operation of the controller 114 branches and loops, as represented by the section 834 enclosed within the dashed line. Within the loop, the system performs several functions simultaneously, namely moving of the dispensing head 128, incrementing the syringe 120, and opening/closing the valve 204 (FIGS. 1, 3). To accomplish this task the output of the stepper chip 430 (FIG. 7) increments the address of the data array at which data is stored, step 836. This provides for automated and sequential access to the data values in the data array. Desirably, the data in the data array may be arranged to cause the system 108 to dispense reagent 130 in a desired pattern, be it sequential or non-sequential, contiguous or non-contiguous. Thus, the dispensing head 128 would only dispense reagent at the specific target locations on the substrate 111 indicated by the dispense data contained in the data array.

Figure 6:
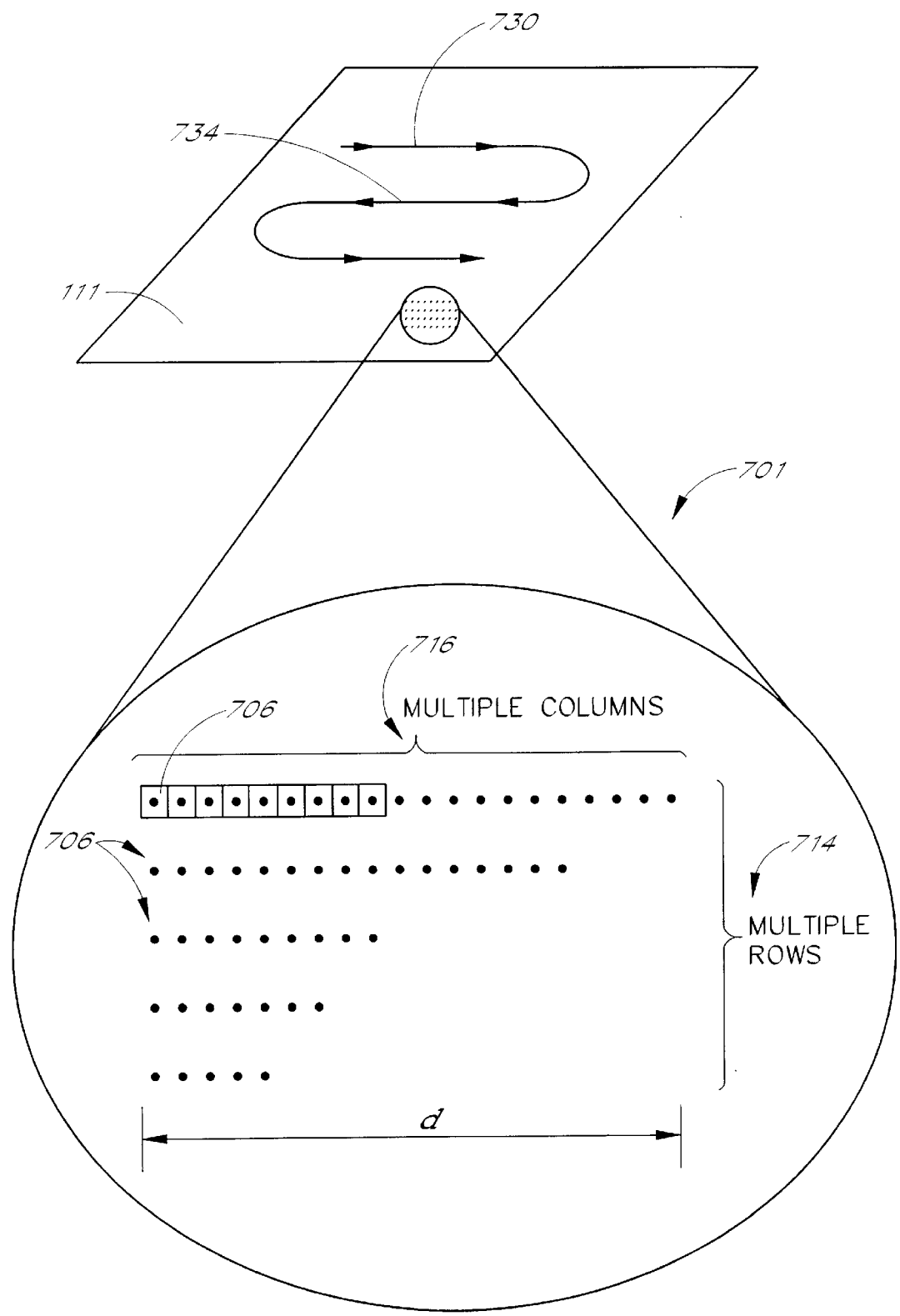
FIG. 6 is a schematic drawing illustrating a preferred method of depositing an array or pattern of reagent onto a substrate and having features and advantages in accordance with one embodiment of the present invention.

The multiplexer 426 (FIG. 7) and miscellaneous registers and logic (FIG. 7) access the syringe increment value 840 and the valve pulse value 844. These values are stored in the static ram array 414 (FIG. 7) and define how the syringe 120 will move and how long the valve 204 (FIG. 3) will remain open for a particular target location 706 (FIG. 6). The syringe increment value is then transferred to a syringe stop count circuit, step 848. Simultaneously, the valve pulse value is transferred to a valve firing circuit, step 852. The sub-routines performed by these circuits control the operation of the syringe 120 and valve 128 (both shown in FIG. 1) respectively. The operation of the syringe stop count circuit 848 and the valve firing circuit 852 are described below in more detail.

After the operation of the syringe stop count circuit 848 and the valve firing circuit 852, the controller 114 queries for additional X axis data at step 854. If additional X axis data exists the system returns to step 836 to increment the address of the data array and repeat the above-described process. Conversely, if no additional data exist for a particular row, the controller 114 pauses the stepper control chip output, step 856, and queries whether additional rows of reagent 130 need to be dispensed, step 860. If data corresponding to additional rows exists in the data array, then the system increments the Y axis motor to thereby advance the dispensing head 128 (FIG. 1) one row, step 862, and returns to step 828 to dispense another row of reagent 130.

If no additional data items exist, i.e. the last X location on the last row has been dispensed, then the controller 114 stops operation. The operator may then load another substrate 111, step 864, and repeat the dispensing process or input another dispensing pattern via the host CPU 402. Alternatively, the dispensing apparatus 108 (FIG. 1), if equipped with an automatic substrate feed (not shown), may automatically load another substrate 111 upon completion of the process.

Figure 9B:
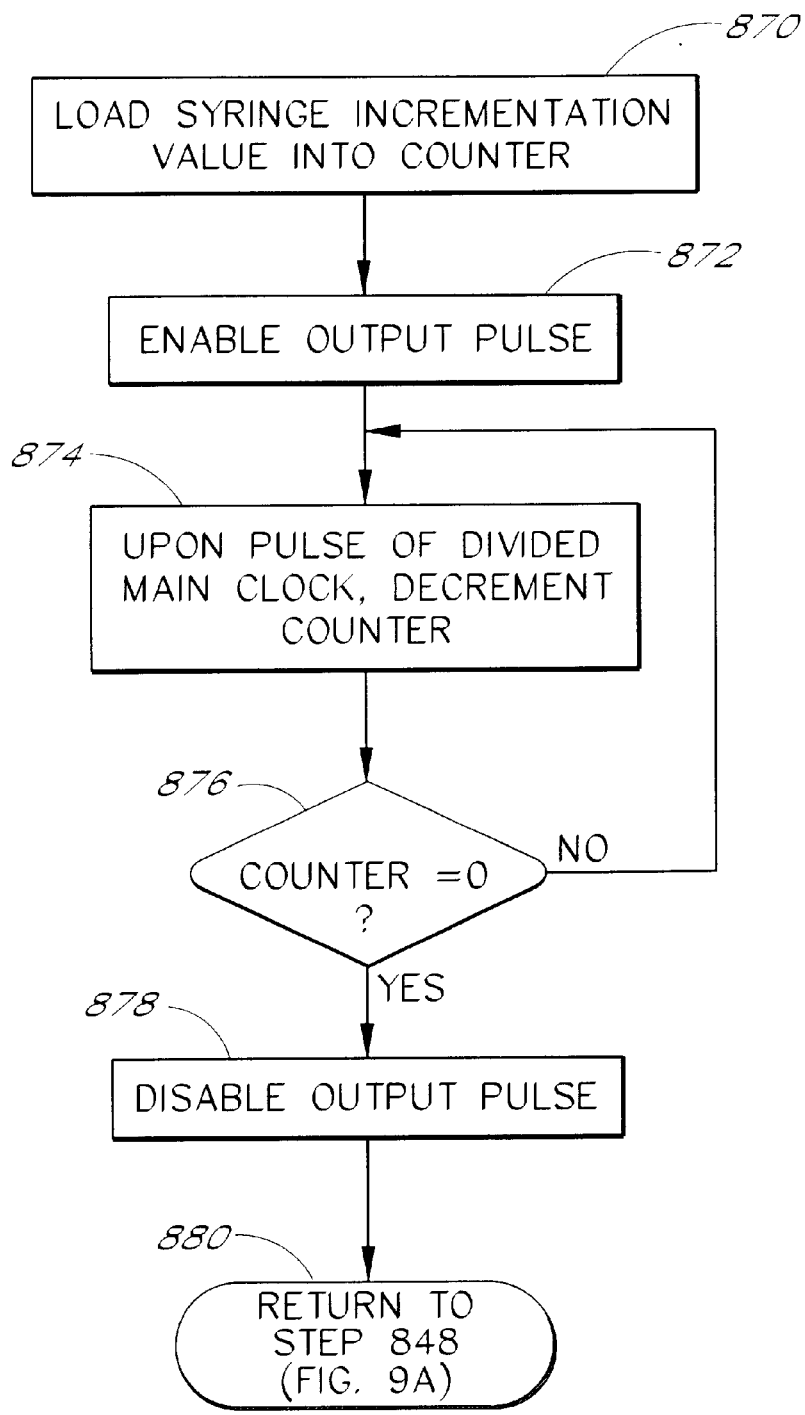

FIG. 9B illustrates, in more detail, the preferred operation of the syringe stop count circuit 408 (FIG. 7). The syringe stop count circuit 408, shown in hardware in FIG. 7, controls the operation of the syringe 120 based on the values in the data array and the operation of the rest of the controller 114. In operation, the syringe increment value, obtained from the data array, loads into the syringe counter 456 (FIG. 7), step 870. If the syringe increment value is a non-zero value, the output of the counter 456 goes high to thereby enable the operation of the syringe driver, step 872. Each clock pulse of the divided stepper chip output 450 (FIG. 7) simultaneously increments the syringe 120 and decrements the counter 456, step 874. In this repeating fashion, the syringe plunger 118

(FIG. 1) moves or advances to thereby increase the pressure in the line 150 (FIG. 1).

At step 876 the controller or host CPU queries the status of the counter 456. If the value of the counter has not reached zero, then the syringe stop count circuit 408 (FIG. 7) maintains the state of the counter output, in this embodiment high or enabled. As a result, the syringe 120 increments on the next divided main clock pulse and the counter decrements, step 874. Alternatively, if the query step determines that the counter value is zero, the output of the counter 456 is disabled, step 878, which in turn halts the advancement of the syringe 120. This completes the operation of the syringe for a particular target location. The operation of the controller 114 returns to FIG. 9A. The above described process repeats for each target location 706 (FIG. 3) on the substrate 111.

Figure 9C:
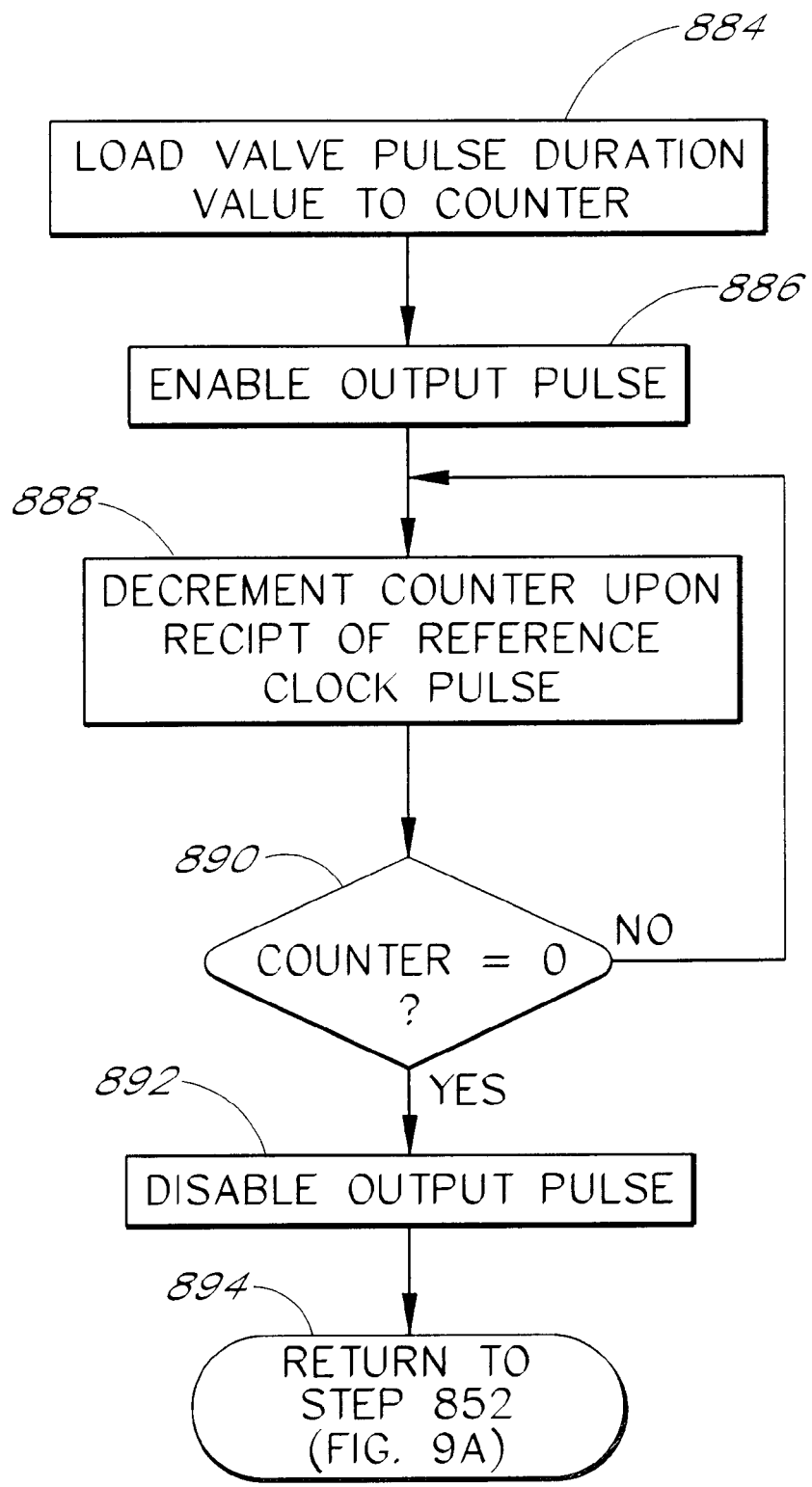

FIG. 9C illustrates, in more detail, the preferred operation of the valve firing circuit 412. The dashed line 412, valve firing circuit 412, shown in hardware in FIG. 7, comprises the hardware enclosed by the dashed line. In operation, the transferred valve pulse value loads into the valve counter 480 (FIG. 7), step 884. If the valve pulse duration is a non-zero value, the output of the counter 480 goes high to thereby enable the operation of the valve driver 484 (FIG. 7), shown at step 886.

Preferably, the valve pulse counter 480 (FIG. 7) operates in relation to a reference clock 482 (FIG. 7) to establish the reference period for the valve operation in units of time instead of number of pulses of the stepper control chip 430 (FIG. 7). Thus, the data array provides information on how many reference clock pulses the valve 204 (FIG. 3) will remain open, which corresponds to a period of time and not the distance traveled by the X-axis stepper motor 123 (FIG. 1). For example, if each clock pulse lasts 0.001 seconds, then programming the valve to remain open for 100 reference clock pulses will result in the valve remaining open for 0.1 seconds or 1/10 of a second.

The valve firing circuit decrements the counter 480 on the next rising edge of the reference clock, step 888. This completes one clock cycle. Next, at step 890, a query is made regarding the status of the counter. If the value of the counter 480 is non-zero, the valve firing circuit 412 maintains the state of the counter output, i.e., high or valve open. As a result, the valve 204 (FIGS. 1, 3) remains open and the counter 480 decrements on the next rising edge of the reference clock pulse, step 888.

Alternatively, if the query step 890 determines that the counter value equals zero, the output of the counter 480 (FIG. 7) is disabled, step 892, which in turn disables the driver 484 (FIG. 7) and causes the valve 204 to close. This completes the valve operation for a particular target location 706. The operation of the system progresses in the fashion described in FIG. 9A step 894. The above described process repeats for each target location 706 (FIG. 6) on substrate 111.

In an alternative embodiment the present invention may be configured to perform selective reagent dispensing operations. For example, instead of configuring the system 108 for continuous linear motion of the dispensing head 128, the system can also provide for random access addressing of substrate target areas. Thus, the dispensing apparatus 108 could, for example, dispense reagent at the upper right hand corner of a substrate 111 and then move to the lower left hand corner and dispense reagent without necessarily dispensing at any locations therebetween. The order and pattern of dispensing is automatically controlled via the data array or manually through the host CPU 402 (FIG. 7). An operator would configure the data array values to create a desired pattern of dispensed reagent 130. This pattern could provide, for example, a symbolic or textual representation indicating the test result, or form a visible brand or trade name on the substrate 111.

Alternative Configurations

While the invention has been described above in connection with a particular preferred embodiment, those skilled in the art will recognize that it may be implemented in any one of a number of alternative configurations, such as a software based system. For example, in a software based system one or more EPROMs could store the computer code. Each EPROM could connect to one or more microprocessors each of which would connect to one or more drivers to provide the appropriate signal to each electromechanical device.

Alternatively, multiple dispensers 502 may be used either in parallel, as illustrated in FIG. 2, or independently of one another. Arrays of dispenser heads could also be configured together, spaced, for example, on 4.5 mm or 9 mm center-to-center, so as to provide array dispensing of 8, 16 or 64 drops simultaneously and/or in synchronous coordination. FIG. 2 illustrates a single continuous feed platform 500 configured with multiple dispensers 512 to handle one or more reagents. This particular dispensing apparatus configuration has significant advantages for continuous web production applications since one or more syringe pumps 512 can be operated in alternating succession while allowing the non-dispensing syringe pump to draw additional reagent from the reservoir or they can be configured independent of one another to dispense the same or different reagents simultaneously or in succession.

A dispensing apparatus constructed in accordance with the present invention may also be mounted on any one of a number of other types of membrane placement and handling modules. Such dispensing platforms may be microprocessor-based and are preferably controlled through an industry standard input/output I-O controller (not shown), such as an RS232 interface. The invention is also well suited for use with individual membrane strip handling modules and continuous reel-to-reel handling modules. For example, an individual membrane strip module may incorporate only X-axis table motion for dispensing. The reel-to-reel platform may incorporate a constant-speed membrane transport with optional mountings attached for motion of one or more dispensers. A drying oven (not shown) may also be used with any of the described embodiments to increase production throughput, as desired.

Use and Operation

FIG. 6 shows a schematic view of a substrate 111, including an enlarged view illustrating how individual "dots" or droplets 702 might preferably be arranged on the substrate 111. Conceptually, the substrate 111 is divided into rows (X-axis) 714 and columns (Y axis) 716 having a predetermined resolution in terms of a number of addressable target areas 706 per linear distance "d". Thus, a linear distance d equal to one inch (2.54 cm) of substrate 111 traveling along one axis may, for example, contain 100–500 or more individually addressable target locations. Each target location would correspond to a number of X-axis stepper motor increments and a number of Y-axis stepper motor increments relative to a predetermined "zero" position.

Because each target location 706 has a unique address, a controller is able to precisely select particular target location (s) in which to dispense predetermined quantities or droplets of reagent. FIG. 6 illustrates one preferred pattern of dispensing motion in relation to the substrate 111. This pattern advantageously decreases the time to complete a particular dispensing operation. Upon executing a first linear pass 730 along a first row, the dispensing head reverses direction and executes a second pass 734 along an adjacent second row. Such bi-directional dispensing advantageously decreases the time required to complete a dispensing operation in comparison to a unidirectional dispensing operation. It is also envisioned that for non-sequential or intermittent dispensing the controller would speed operation by dispatching the dispensing head directly to or adjacent the next desired target location without necessarily completing each successive pass or each intervening row.

Another significant advantage achieved by the invention is the ability to define the desired output data or reagent pattern in a more user-friendly and easy to understand format, such as a simple bit map or computer graphics file. As known by those skilled in the computer graphics art, bit map graphics files are easily generated and stored using any number of commercially available software editing programs, such as PC-Paint™ or the like. Modified graphics software specific to the implementation of this invention can also be provided for inputting and recording other relevant data, such as desired reagent density, droplet size, droplet velocity, and the like, for each particular dot address. The data file comprising the bit map can then be easily downloaded directly to a controller which, using suitable software and control techniques, directs the dispensing apparatus to create the desired reagent pattern having the specified characteristics.

The use and operation of the invention as described above is simply one preferred mode of use and operation of the present invention. Many other modes of operation are also possible having significant commercial and scientific advantages, as will be apparent to those skilled in the art. Several of these additional preferred modes of operation are described below by way of specific examples and illustrations:

EXAMPLE 1

PROGRAMMED LINE MODE

Figure 10A:
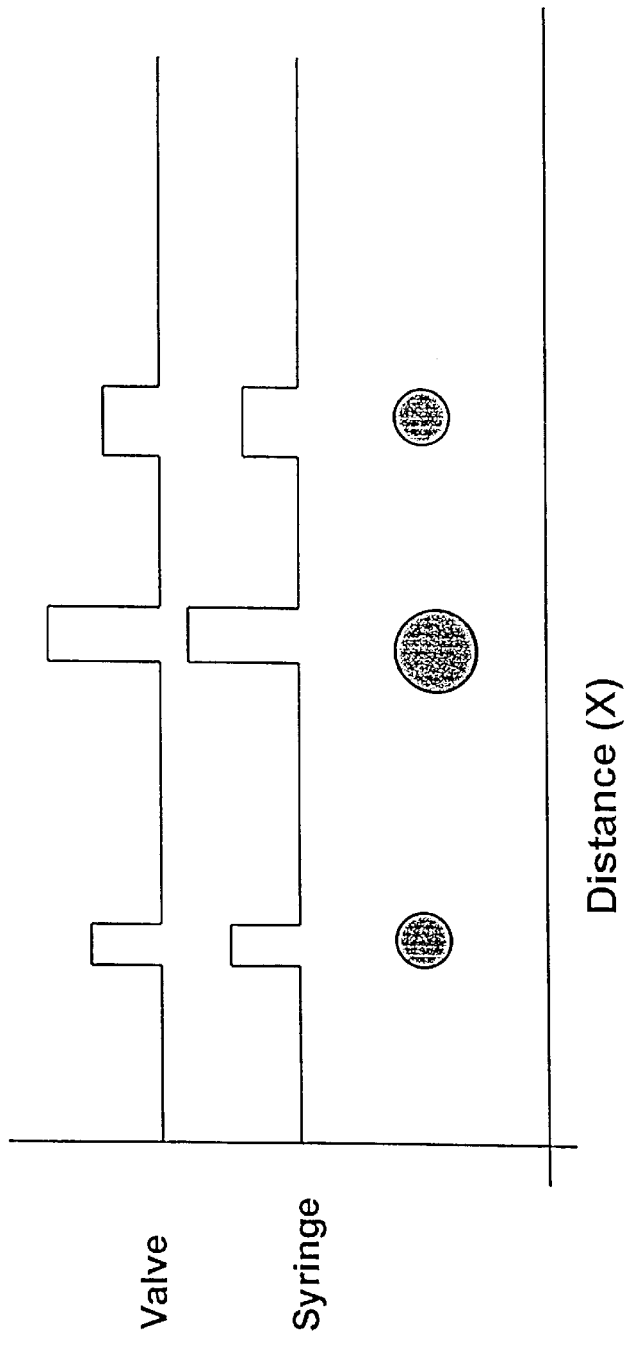
FIG. 10A is a schematic drawing illustrating an example of programmed mode line dispensing in accordance with one embodiment of the present invention, such as for creating custom dot array patterns on a membrane or glass slide.

FIG. 10A is a schematic drawing illustrating a programmed line mode of dispense operation in accordance with one embodiment of the present invention. In this mode, individual dots of the same or different amounts of fluid may be dispensed at different positions along a linear or non-linear path. The individual dots may or may not be colinear or evenly spaced, as desired. They may be spaced or offset from one another by a desired amount of spacing. This mode of operation may be useful, for example, for creating custom dot array patterns on a membrane or glass slide.

EXAMPLE 2

SYNCHRONIZED LINE MODE

Figure 10B:
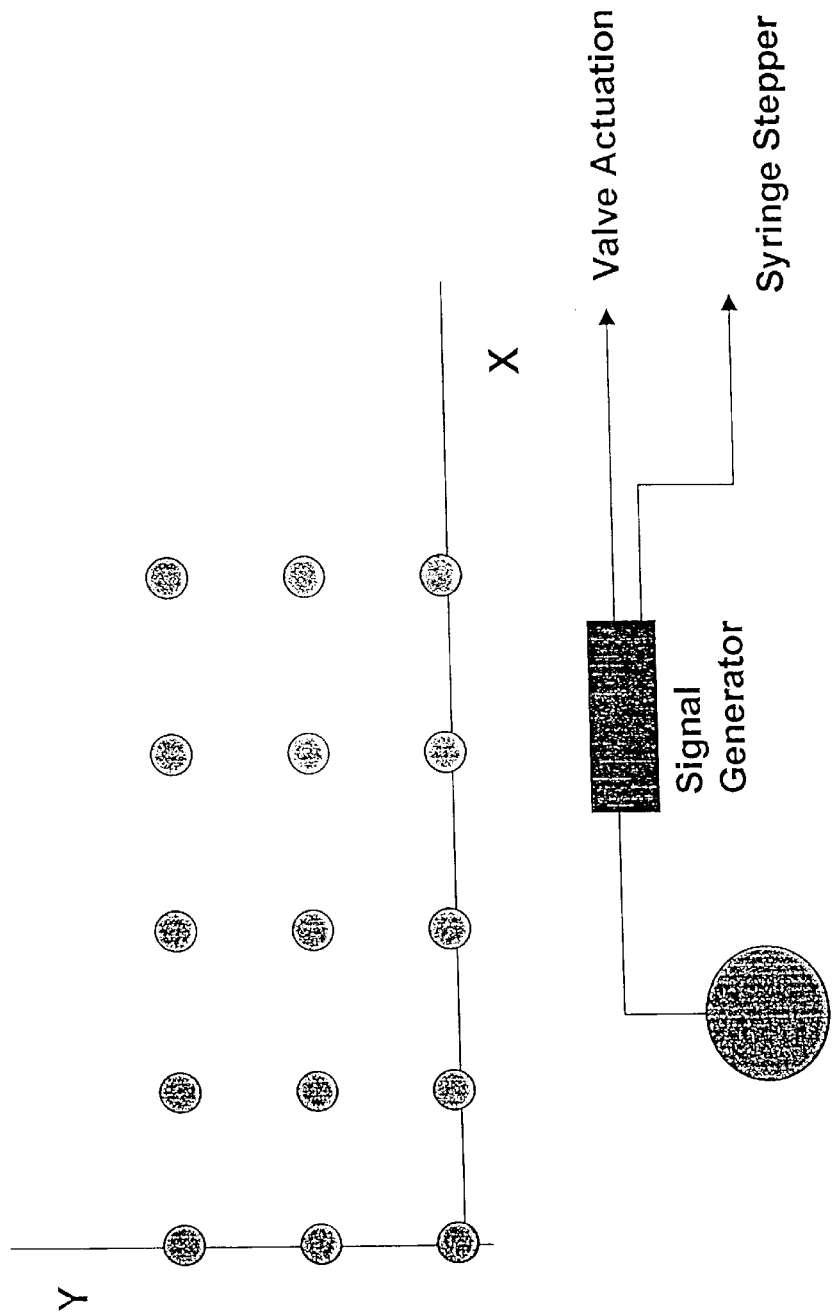
FIG. 10B is a schematic drawing illustrating an example of synchronized line dispensing in accordance with one embodiment of the present invention, such as for creating high-density dot arrays on a membrane or glass slide.
Figure 10C:
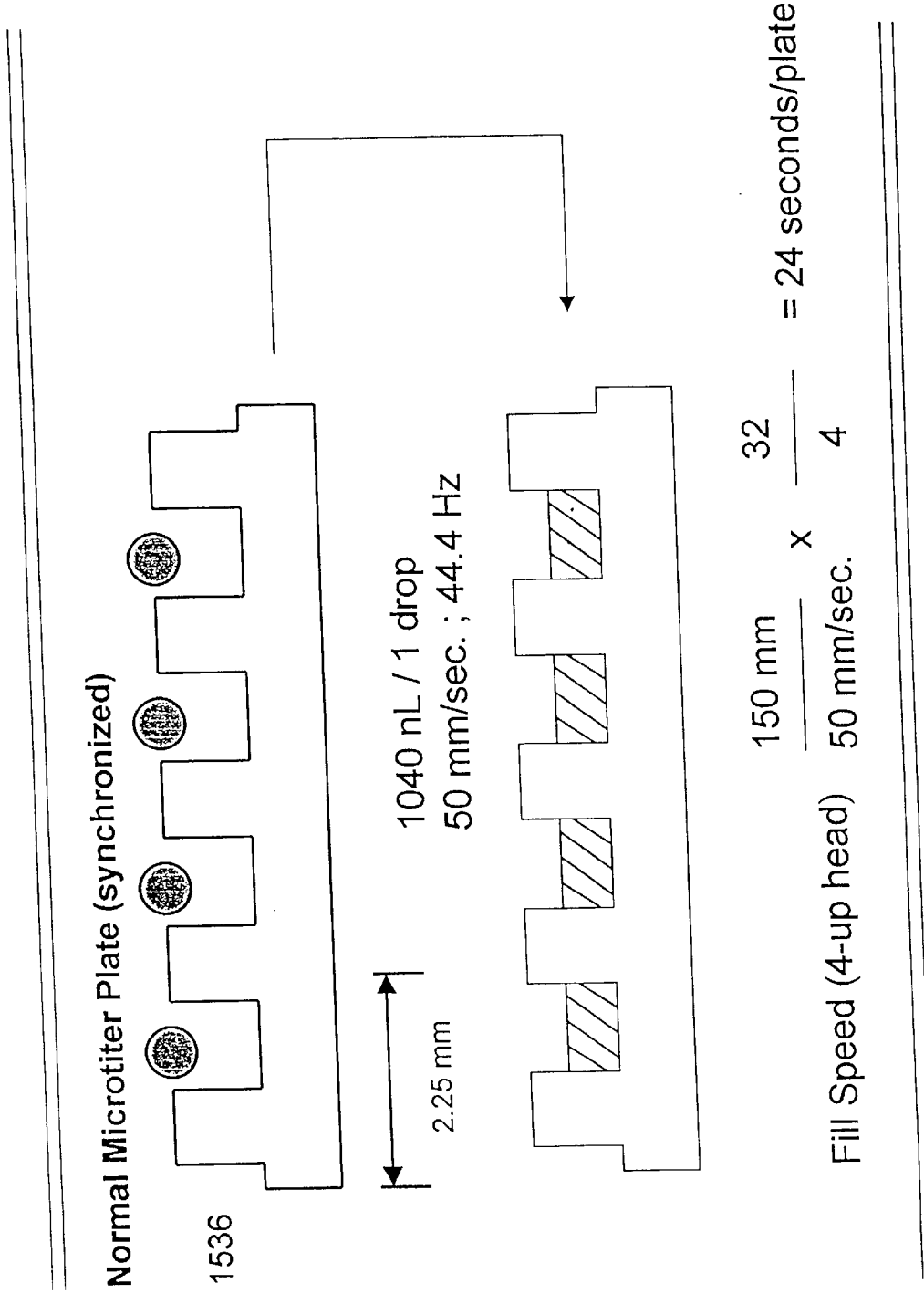
FIG. 10C is a schematic drawing illustrating an example of synchronized line dispensing in accordance with one embodiment of the present invention such as for filling conventional micro-well plates.

FIG. 10B is a schematic drawing illustrating a synchronized mode of line dispense operation in accordance with one embodiment of the present invention, such as for creating high-density dot arrays on a membrane or glass slide. This mode of dispense operation is particularly suited for dispensing reagent or other fluids into a conventional well plate array, such as illustrated in FIG. 10C, using either a single or multi-head dispenser. For example, a standard 96-well (8×12) well plate may be filled using a multi-head dispenser having a 1×8 dispense head array. The dispenser would dispense 8 parallel lines of 12 drops each with a spacing of 9 mm between drops and a line length of 99 mm. For a 1536-well (32×48) well plate array the same dispenser could be used to dispense 8 parallel lines of 48 drops each with a spacing of 2.25 mm between drops and a line length of 105.75 mm. The line pattern would be repeated 4 times to fill the well plate.

The same dispense mode could also be used to dispense droplet patterns onto an electronic biosensor array. These are usually fabricated using printed arrays of sensors or electrodes on a substrate. In this case the reagent is dispensed so as to match the sensor pattern. Again this can be done using a line mode similar to the case of the conventional micro-well plate as described above.

EXAMPLE 3

NON-SYNCHRONIZED LINE MODE

Figure 10D:
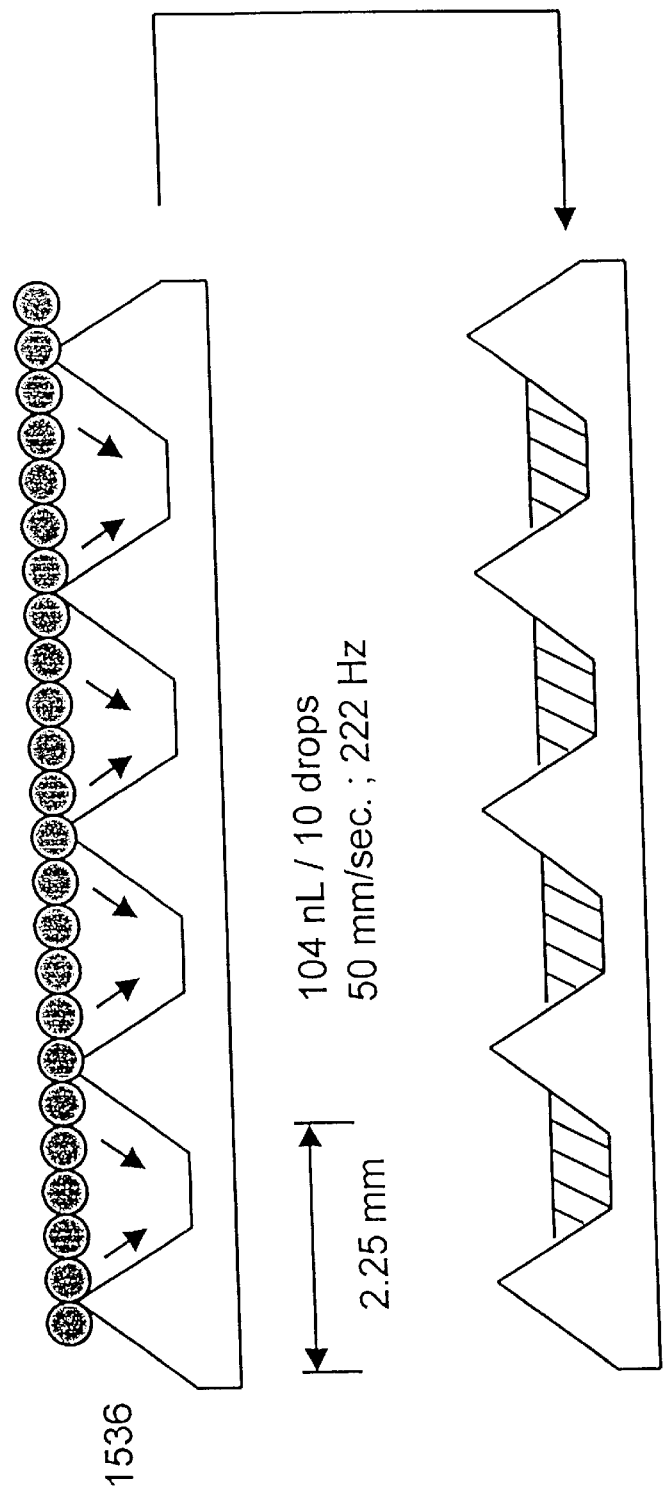
FIG. 10D is a schematic drawing illustrating an example of non-synchronized line dispensing in accordance with one embodiment of the present invention such as for filling vision micro-well plates.

FIG. 10D is a schematic drawing illustrating a non-synchronized mode of line dispense operation in accordance with one embodiment of the present invention such as for creating continuous uniform lines on a flat substrate or for filling wells in a vision micro-well plate. A vision micro-well plate uses wells having an angular apex that separates each well. When dispensing a uniform continuous line of reagent the individual drops roll off the apex into the adjacent wells thus giving statistically accurate and even filling of wells.

The present invention improves the ability to dispense uniform lines by eliminating communication and acceleration/deceleration problems. Conventional dispensing systems suffer from a lack of uniformity in the spacing of droplets at the start and finish of a line forming operation. Uniformity is very important, particularly when dispensing short lines because the effects of starting and finishing each line can dominate the quality of the entire array if composed of short lines. This could cause unacceptable statistical variances, for example, when using a vision micro-well plate.

In the non-synchronized mode of line dispense operation the valve dispense head and syringe pump operate at some harmonic of the motion stepper to produce a series of drops. For every N steps of the motion stepper one drop is dispensed. For example, if the motion stepper has a resolution of about 2 microns and the syringe pump has a resolution of 192,000 steps per full stroke then to dispense a 20.8 nL drop every 0.5 mm using a 100 uL syringe then N=250 and M=40. Therefore, the amount of droplets dispensed per unit of linear motion can be precisely controlled. For simultaneous X and Y motion, such as for forming a diagonal line, fairly simple adjustments can be made to the dispensing frequency to ensure the desired number of drops per unit of linear distance.

EXAMPLE 4

DOT ARRAY MAPPING

Figure 10E:
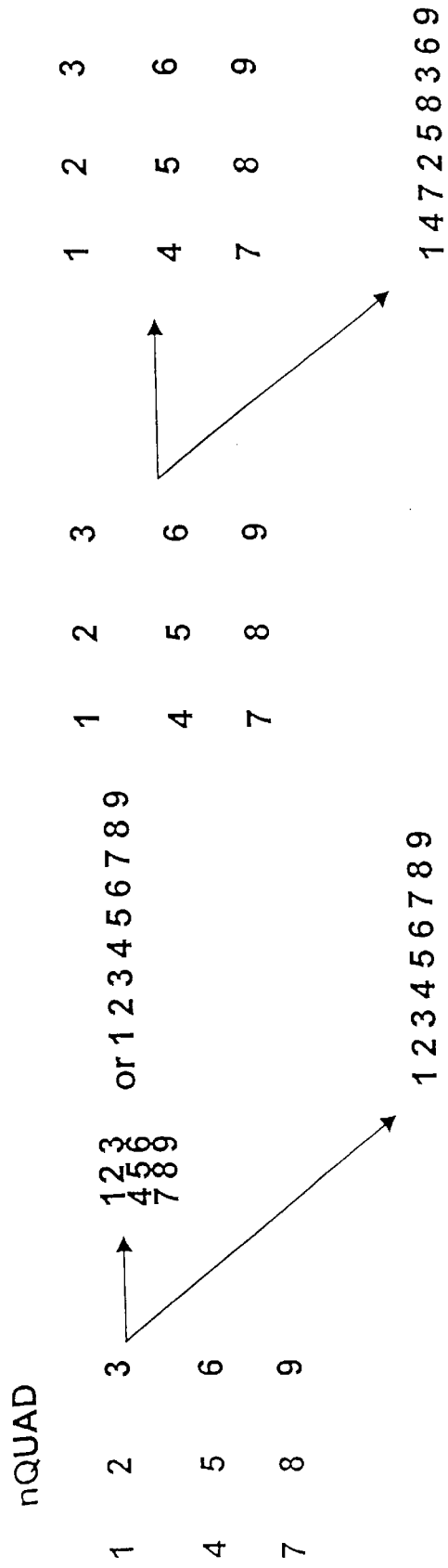
FIG. 10E is a schematic drawing illustrating an example of dot array mapping in accordance with one embodiment of the present invention, such as for mapping one or more micro-well plates onto a slide or other substrate.

FIG. 10E is a schematic drawing illustrating a preferred mode of dot array mapping in accordance with one embodiment of the present invention. For example, it is often desirable to map (replicate or transform) one or more microplate arrays into a high density array on a membrane or glass slide. For instance, one could map sixteen 96-well well plates having 9 mm center-to-center well spacings into a single 1536 dot array having center-to-center spacings in the range of 100–1000 microns.

This task can be accomplished several ways using the invention disclosed herein. One example would be to successively operate one head at a time of a 8-head dispenser with 9 mm center-to-center head spacing using a synchronous line dispense mode with a large spacing between drops. For example, a common substrate is a standard 25×76 mm microscope slide. One can array 50 glass slides on an X-Y table and operate each of the 8 heads in succession to produce drops with a spacing in the range of 25 mm on each slide at the same position. The other 7 heads can be operated in linear succession with small offsets to produce an array of 8 dots on the glass slides with a small separation of between about 100–1000 microns between dots. Note that this operation can be done using one head at a time or, more preferably, using all 8 heads dispensing in rapid succession with small time delays to provide the desired linear spacing. By repeating this function for all sixteen plates and using suitable offsets one can map the sixteen well plates into a single 1526 array on each glass slide. In this case the map would be a miniaturized replica of each 96 well plate located in a 4×4 array.

The dispenser can also be programmed so as to transform one or more well plate arrays into a new or different high or low density array. For example, a series of two dimensional arrays may be transformed into rows or columns of a larger high-density array, or arrays may be transposed or inverted. Direct 1:1 mapping can also be achieved by operating the dispense heads in parallel synchronous line mode to produce 8 drops on each slide with a spacing of 9 mm. Other modes and variations for the use and operation of the invention will be apparent to those skilled in the art.

Although this invention has been disclosed in the context of certain preferred embodiments and examples, it will be understood by those skilled in the art that the present invention extends beyond the specifically disclosed embodiments to other alternative embodiments and/or uses of the invention and obvious modifications and equivalents thereof. Thus, it is intended that the scope of the present invention herein disclosed should not be limited by the particular disclosed embodiments described above, but should be determined only by a fair reading of the claims that follow.

What is claimed is:

1. An apparatus for dispensing desired patterns of liquid reagent onto a receptive substrate, comprising:

a dispensing head having an inlet end and an outlet end, said dispensing head being responsive to a first signal comprising electrical pulses having a frequency and duration to dispense droplets of said liquid reagent onto said substrate, said substrate and/or said dispensing head being secured in association with a table or carriage responsive to a second signal comprising electrical pulses having a frequency and duration to provide relative X, X-Y or X-Y-Z motion between said substrate and said dispensing head;

a pump device, responsive to a third signal comprising electrical pulses having a frequency and duration, for supplying a quantity of said liquid reagent to the inlet end of said dispensing head, said pump device being hydraulically arranged in series with said dispensing head so as to independently regulate the amount or flow rate of said liquid reagent supplied to said dispensing head; and a controller adapted to receive data representative of a desired reagent pattern and to output and coordinate said first, second and third signals so as to cause relative motion between said substrate and said dispensing head and simultaneously to cause said pump device and said dispensing head to dispense said droplets of said liquid reagent at one or more desired locations on said substrate to form said desired reagent pattern, and wherein said controller is adapted to adjust the phase of said first and third signals relative to said second signal in order to compensate for the magnitude of said relative motion between said substrate and said dispensing head given the probable trajectory of each said droplet of liquid reagent.

2. The apparatus of claim 1 wherein said dispensing head comprises a valve adapted to be opened and closed at a predetermined frequency and duty cycle in response to said first signal so as to dispense said droplets of liquid reagent.

3. The apparatus of claim 2 wherein said valve is actuated by an electric solenoid or piezoelectric constrictor device.

4. The apparatus of claim 2 wherein the frequency and duty cycle of said valve can each be adjusted substantially independently for a given quantity or flow rate of said liquid reagent to produce said droplets having a desired size, frequency and/or exit velocity.

5. The apparatus of claim 1 wherein said dispensing head comprises an air brush dispenser adapted to form an aerosol having a predetermined mist quality and spray pattern in response to said first signal so as to dispense said droplets of liquid reagent.

6. The apparatus of claim 1, wherein said pump device comprises a direct current fluid source.

7. The apparatus of claim 6 wherein said direct current fluid source comprises a positive displacement syringe pump and a stepper motor adapted to cause said pump to dispense predetermined incremental quantities or flow rates of said liquid reagent to said dispensing head.

8. The apparatus of claim 7 further comprising a second positive displacement syringe pump hydraulically coupled to said first positive displacement pump for providing continuous flow capability.

9. The apparatus of claim 1 wherein said controller is further adapted to output and coordinate said first and third signals to achieve a predetermined or steady-state dispense pressure prior to initiating dispensing operation.

10. The apparatus of claim 1 wherein said controller is adapted to receive data in the form of a graphic bit map representative of a desired reagent pattern.

11. The apparatus of claim 1 wherein said controller is adapted to advance the phase of said first and third signals relative to said second signal in order to compensate for the magnitude of said relative motion between said substrate and said dispensing head.

12. The apparatus of claim 1 wherein said controller is adapted to advance or retard the phase of said first and third signals relative to said second signal in order to compensate for the viscosity, adhesion coefficient, temperature, pressure or density of said liquid reagent.

13. The apparatus of claim 1 wherein said controller is adapted to advance or retard the phase of said first and third signals relative to said second signal by a predetermined amount determined to reduce or minimize dispensing inaccuracies or errors for a given reagent and/or setup.

14. The apparatus of claim 1 wherein said controller is adapted to advance or retard the phase of said first signal relative to said third signal by a predetermined amount determined to provide desired drop offsets and/or to optimize dispensing operation.

15. An apparatus for high-speed precision dispensing of liquid reagents onto a receptive substrate, comprising:

a dispenser responsive to a first signal to dispense droplets of said liquid reagent onto said receptive substrate;

a table or carriage responsive to a second signal to provide relative X, X-Y or X-Y-Z motion between said substrate and said dispenser; and a controller adapted to receive data representative of a desired dot-matrix reagent pattern and to provide said first and second signals for causing relative motion between said substrate and said dispenser while simultaneously causing said dispenser to dispense said droplets of said liquid reagent at one or more desired locations on said substrate to form said desired reagent pattern, said controller being further adapted to adjust the phase lag or lead between said first and second signals in order to provide desired offsets and/or to compensate for the magnitude of said relative motion between said substrate and said dispensing head given the probable trajectory of each said droplet, whereby high-speed precision dispensing is achieved.

16. The apparatus of claim 15 wherein said dispenser comprises a valve adapted to be opened and closed at a predetermined frequency and duty cycle in response to said first signal so as to dispense said droplets of liquid reagent.

17. The apparatus of claim 16 wherein said valve is actuated by an electric solenoid.

18. The apparatus of claim 16 wherein the frequency and duty cycle of said valve can each be adjusted substantially independently for a given quantity or flow rate of said liquid reagent to produce said droplets having a desired size, frequency and/or exit velocity.

19. The apparatus of claim 15 wherein said controller is adapted to receive data in the form of a graphic bit map representative of said desired reagent pattern.

20. The apparatus of claim 15 wherein said first and second signals comprise electrical pulses having a frequency and duration.

21. The apparatus of claim 20 wherein said controller is adapted to advance the phase of said first signal relative to said second signal in order to compensate for the magnitude of said relative motion between said substrate and said dispenser.

22. The apparatus of claim 20 wherein said controller is adapted to advance or retard the phase of said first signal relative to said second signal in order to compensate for the viscosity, adhesion coefficient, temperature, pressure or density of said liquid reagent.

23. The apparatus of claim 20 wherein said controller is adapted to advance or retard the phase of said first signal relative to said second signal by a predetermined amount determined to reduce or minimize dispensing inaccuracies or errors for a given reagent and/or set up.

24. The apparatus of claim 15 further comprising a pump device responsive to a third signal for supplying a quantity of said liquid reagent to said dispenser, said pump device being hydraulically arranged in series with said dispenser so as to regulate the amount or flow rate of said liquid reagent supplied to said dispenser.

25. The apparatus of claim 24 wherein said pump device comprises a direct current fluid source.

26. The apparatus of claim 25 wherein said direct current fluid source comprises a positive displacement syringe pump and a stepper motor adapted to cause said pump to dispense predetermined incremental quantities or flow rates of said liquid reagent to said dispenser.

27. The apparatus of claim 24 wherein said controller is further adapted to output and coordinate said first and third signals to achieve a predetermined or steady-state dispense pressure prior to initiating dispensing operation.

* * * * *

UNITED STATES PATENT AND TRADEMARK OFFICE
CERTIFICATE OF CORRECTION

PATENT NO. : 6,063,339
DATED : May 16, 2000
INVENTOR(S) : Thomas C. Tisone et al.

It is certified that error appears in the above-identified patent and that said Letters Patent is hereby corrected as shown below:

Column 1,
Line 5, "1988" should read -- 1998 --.

Signed and Sealed this

Twenty-eighth Day of January, 2003

JAMES E. ROGAN
*Director of the United States Patent and Trademark Office*